(12) United States Patent
Harley et al.

(10) Patent No.: US 7,846,904 B2
(45) Date of Patent: Dec. 7, 2010

(54) COMPOSITIONS AND METHODS FOR INCREASING TELOMERASE ACTIVITY

(75) Inventors: Calvin Bruce Harley, Murphys, CA (US); Allison C. Chin, Stanford, CA (US); Tsutomu Akama, Sunnyvale, CA (US); Nancy Yuk-yu Ip, Kowloon (HK); Yung-hou Wong, Kowloon (HK); David M. Miller-Martini, Ridgway, PA (US)

(73) Assignee: Geron Corporation, Menlo Park, CA (US)

( * ) Notice: Subject to any disclaimer, the term of this patent is extended or adjusted under 35 U.S.C. 154(b) by 597 days.

(21) Appl. No.: 10/562,374

(22) PCT Filed: Jun. 23, 2004
(Under 37 CFR 1.47)

(86) PCT No.: PCT/US2004/020277

§ 371 (c)(1),
(2), (4) Date: Mar. 9, 2007

(87) PCT Pub. No.: WO2005/000245

PCT Pub. Date: Jan. 6, 2005

(65) Prior Publication Data

US 2008/0113925 A1 May 15, 2008

Related U.S. Application Data

(60) Provisional application No. 60/480,988, filed on Jun. 23, 2003.

(51) Int. Cl.
*A61K 31/56* (2006.01)
*A01N 45/00* (2006.01)

(52) U.S. Cl. .......................................... 514/26; 514/169
(58) Field of Classification Search .................. None
See application file for complete search history.

(56) References Cited

U.S. PATENT DOCUMENTS

| | | | |
|---|---|---|---|
| 5,629,154 | A | 5/1997 | Kim et al. |
| 5,663,160 | A | 9/1997 | Meybeck et al. |
| 5,770,578 | A | 6/1998 | Binder et al. |
| 5,785,977 | A | 7/1998 | Breithbarth |
| 5,786,343 | A | 7/1998 | Ber |
| 5,916,565 | A | 6/1999 | Rose et al. |
| 5,942,233 | A | 8/1999 | Chang |
| 6,007,989 | A | 12/1999 | West et al. |
| 6,126,942 | A | 10/2000 | Yang |
| 6,153,208 | A | 11/2000 | McAtee et al. |
| 6,162,459 | A | 12/2000 | Hu |
| 6,171,604 | B1 | 1/2001 | Mousa |
| 6,190,678 | B1 | 2/2001 | Hasenoehrl et al. |
| 6,277,396 | B1 | 8/2001 | Dente |
| 6,346,539 | B1 | 2/2002 | Raman et al. |
| 6,696,094 | B2 | 2/2004 | Wu |
| 6,855,344 | B2 | 2/2005 | Chou |
| 2002/0044977 | A1 | 4/2002 | Close |
| 2002/0164387 | A1 | 11/2002 | Wei et al. |
| 2002/0182272 | A1 | 12/2002 | Halstead |
| 2003/0108629 | A1 | 6/2003 | Chou |
| 2007/0042962 | A1 | 2/2007 | Adams |
| 2007/0122501 | A1 | 5/2007 | Harley et al. |
| 2007/0154435 | A1 | 7/2007 | Harley |

FOREIGN PATENT DOCUMENTS

| | | |
|---|---|---|
| CN | 1283462 A | 2/2001 |
| CN | 1079265 C | 2/2002 |
| CN | 1383853 A | 12/2002 |
| CN | 1406585 A | 4/2003 |
| JP | 62-012791 | 1/1987 |
| WO | WO 99/35243 A3 | 7/1999 |
| WO | WO 00/08135 A1 | 2/2000 |
| WO | WO 00/31238 A2 | 6/2000 |
| WO | WO 01/01996 A1 | 1/2001 |
| WO | WO 02/091999 A2 | 11/2002 |
| WO | WO 02/91999 A2 | 11/2002 |
| WO | WO 2005/000245 A2 | 1/2005 |
| WO | WO 2005/000248 A2 | 1/2005 |
| WO | WO 2005/044179 A2 | 5/2005 |

OTHER PUBLICATIONS

"Astragalus" www.drugs.com/npp/astragalus.html, 5 pages (Oct. 20, 2008).

Bedir, E. et al., "Cycloartane triterpene glycosides from the roots of *Astragalus brachypterus* and *Astragalus microcephalus*," *J. Nat. Prod.*, 61:1469-72 (1998).

Chu, D-T. et al., "Fractionated extract of *Astragalus membranaceus*, a Chinese medicinal herb, potentiates lak cell cytotoxicity generated by a low dose of recombinant interleukin-2," *J. Clin. Lab. Immunol.*, 26:183-7 (1988).

Chu, D-T. et al., "Immunotherapy with Chinese medicinal herbs. II Reversal of cyclophosphamide-induced immune suppression by administration of fractionated Astragalus membranaceus in vivo," *J. Clin. Lab. Immunol.*, 25:125-9 (1988).

Ionkova, I., "*Astragalus* species (Milk Vetch): in Vitro culture and the production of saponins, astragaline, and other biologically active compounds," Biotechnology in Agriculture and Forestry, vol. 33, Medicinal and Aromatic Plants VIII, Y. Bajaj, Ed., Springer Verlag, Berlin, pp. 97-138 (1995).

Juntao, L. et al., "Effect of retinoic acid and genseng on the telomerase activity in the liver cancer cell," *J. Trop. Med.*, 2(1):39-40 (2002) (English Abstract).

(Continued)

*Primary Examiner*—Elli Peselev
(74) *Attorney, Agent, or Firm*—Leslie A. Mool; David J. Earp

(57) ABSTRACT

The present invention relates to methods for increasing telomerase activity in cells. Such compositions include pharmaceutical, including topical, and nutraceutical formulations. The method and compositions are useful for treating diseases subject to treatment by an increase in telomerase activity in cells or tissue of a patient, such as, for example, HIV infection, various degenerative diseases, and acute or chronic skin aliments. They are also useful for enhancing replicative capacity of cells in culture, as in ex vivo cell therapy and proliferation of stem cells.

14 Claims, 8 Drawing Sheets

OTHER PUBLICATIONS

Xiao, H. et al., "Total analytical method for Radix *Astragali* extract using two-binary multisegment gradient elution liquid chromatography," *J. Sep. Sci.*, 24:186-96 (2001).

Zhao, K. et al., "Enhancement of the immune response in mice by Astragalus membranaceus extracts," *Immunopharmacology*, 20:225-34 (1990).

Zheng, Z. et al., "Studies on chemical constituents and immunological function activity of hairy root of *Astragalus membranaceus*," *Chinese Journal of Biotechnology*, 14(2):L93-7 (1998).

Bedir, E. et al., "Immunostimulatory effects of cycloartane-type triterpene glycosides from *Astragalus* species", *Biol. Pharm. Bull.*, 23(7):834-837 (2000).

Bodnar, A. G. et al., "Extension of life-span by introduction of telomerase into normal human cells" *Science*, 279(5349):349-52 (1998).

Calzada, L. et al., "Effect of tetracyclic triterpenes (argentatins A, B and D) on the estradiol receptor of hormone-dependent tumors of human breast", *Medical Science Research*, 23(12):815-16 (1995).

Chiu, C. P. et al., "Replicative senescence and cell immortality: the role of telomeres and telomerase", *Proc. Soc. Exp. Biol. Med.*, 214(2):99-106 (Feb. 1997).

Dagarag, M. et al., "Differential impairment of lytic and cytokine functions in senescent human immunodeficiency virus type 1-specific cytotox T lymphocytes", *Journal of Virology*, 77(5):3077-83 (2003).

Farwell, D. G. et al., "Genetic and epigenetic changes in human epithelial cells immortalized by telomerase", *American Journal of Pathology*, 156(5):1537-47 (2000).

Fujimoto, R. et al., "Expression of telomerase components in oral keratinocytes and squamous cell carcinomas", *Oral Oncology*, 37(2):132-40 (2001).

Funk, Walter D. et al., "Telomerase expression restores dermal integrity to in vitro- aged fibroblasts in a reconstituted skin model", *Experimental Cell Research*, 258(2):270-278 (2000).

Harle-Bachor, C. et al., "Telomerase activity in the regenerative basal layer of the epidermis inhuman skin and in immortal and carcinoma-derived skin keratinocytes", *Proc. Natl. Acad. Sci. USA*, 93(13):6476-81 (1996).

Harley, C. B. et al., "Telomeres shorten during ageing of human fibroblasts", *Nature*, 345(6274):458-60 (1990).

Henderson, S. et al., "In situ analysis of changes in telomere size during replicative aging and cell transformation", *Journal of Cell Biology*, 134(1):1-12 (1996).

Huang, Y. et al., "Selected non-timber forest products with medicinal applications from Jilin Province in China", Conference Title: Forest communities in the third millennium: Linking research, business, and policy toward a sustainable non-timber forest product sector; Kenora, Ontario, Canada, Oct. 1-4, 1999; General Technical Report- North Central Research Station, USDA Forest Service (No. NC-217): p. 93-101 (2000).

International Search Report for PCT application PCT/US2004/0202777 search report dated Mar. 21, 2005, 2 pages (2005).

Kaneko, M. et al., "Accelerated recovery from cyclophosphamide-induced leukopenia in mice administered a Japanese ethical herbal drug, *Hochu-ekkito*", *Immunopharmacology*, 44(3):223-231 (1999).

Kang, M. K. et al., "Replicative senescence of normal human oral keratinocytes is associated with the loss of telomerase activity without shortening of telomeres", *Cell Growth & Differentiation*, 9(1):85-95 (1998).

Khushbaktova, Z. A. et al.,"Influence of cycloartanes from plants of the genus *Astragalus* and their synthetic analogs on the contractive function of the *myocarbium* and the activity of Na, K-ATPase", *Chemistry of Natural Compounds*, 30(4):469-473 (1994).

Kitagawa et al., Saponin and Sapogenol XXXIV. Chemical Constituents of Astragali Radix, the Root of *Astragalus membranaceus* Bunge (1). Cycloastragenol, the 9,19-Cyclolanostane-type Aglycone of Astragalosides, and the Artifact Aglycone Astragenol, *Chem. Pharm. Bull.*, 31(2):689-697 (1983).

Kitagawa et al., Saponin and Sapogenol XXXV. Chemical Constituents of Astragali Radix, the Root of *Astragalus membranaceus* Bunge (2). Astragalosides I, ll and IV, Acetylastragaloside I and Isoastragalosides I and II, *Chem. Pharm. Bull.*, 31(2):698-708 (1983).

Kinjo, J. et al., "Anti-herpes virus activity of fabaceous triterpenoidal saponins", *Biological & Pharmaceutical Bulletin* 23(7):887-9 (2000).

Lee, K. M. et al., "Immortalization with telomerase of the Nestin-positive cells of the human pancreas", *Biochem Biophys Res Commun*, 301(4):1038-44 (2003).

Mattson, M. P. ,"Emerging neuroprotective strategies for Alzheimer's disease: dietary restriction, telomerase activation, and stem cell therapy", *Experimental Gerontology*, 35(4):489-502 (2000).

Morales, C. P. et al., "Absence of cancer-associated changes in human fibroblasts immortalized with telomerase", *Nature Genetics*, 21(1):115-8 (1999).

Oda, K. et al., "Adjuvant and haemolytic activities of 47 saponins derived from medicinal and food plants", *Biological Chemistry*, 381(1):67-74 (2000).

Oh, H. And Schneider, M. D. ,"The emerging role of telomerase in cardiac muscle cell growth and survival", *Journal of Molecular Cellular Cardiology*, 34(7):717-24 (2002).

Pistelli, L., et al., "Antimicrobial and antifungal activity of crude extracts and isolated saponins from*Astragalus verrucosus*", *Fitoterapia*, 73(4):336-339 (2002).

Simonsen, J. L. et al., "Telomerase expression extends the proliferative life-span and maintains the osteogenic potential of human bone marrow stromal cells", *Nature Biotechnology*, 20(6):592-6 (2002).

Thomas, M. , Yang, L. , and Hornsby, P. J., "Formation of functional tissue from transplanted adrenocortical cells expressing telomerase reverse transcriptase", *Nature Biotechnology*, 18(1):39-42 (2000).

Vasa, M. et al., "Nitric oxide activates telomerase and delays endothelial cell senescence", *Circulation Research*, 87(7):540-542 (2000).

Wang, Y-P. et al., "Effect of astragaloside IV on T, B lymphocyte proliferation and peritoneal macrophage function in mice", *Acta Pharmacologica Sinica*, 23(3): 263-6 (2002).

Yang, J. et al., "Telomerized human microvasculature is functional in vivo", *Nature Biotechnology*, 19(3):219-24 (2001).

Yang, J., et al., "Human endothelial cell life extension by telomerase expression", *The Journal of Biological Chemistry*, 274(37):26141-26148 (1999).

Yasukawa, K. et al., "Sterol and triterpene derivatives from plants inhibit the effects of a tumor promoter, and sitosterol and betulinic acid inhibit tumor formation in mouse skin two-stage carcinogenesis", *Oncology*, 48(1) :72-6 (1991).

Yudoh, K. et al., "Reconstituting telomerase activity using the telomerase catalytic subunit prevents the telomere shorting and replicative senescence in human osteoblasts", *Journal of Bone and Mineral Research*, 16(8):1453-1464 (2001).

Zhang W. J. et al., "Regulation of the fibrinolytic potential of cultured human umbilical vein endothelial cells : astragaloside IV downregulates plasminogen activator inhibitor-1 and upregulates tissue-type plasminogen activator expression", *Journal of Vascular Research*, 34(4):273-80 (1997).

Zi-Pu, L. And Qian, C., "Effects of astragaloside IV on myocardial calcium transport and cardiac function in ischemic rats", *Acta Pharmacol Sin* 23(10):898-904 (2002).

Chen, J. & Chen, T., "Huang Qi (Radix Astragali)," *Chinese Medical Herbology and Pharmacology*, Chapter 17 Tonic Herbs, Art of Medicine Press, Inc., pp. 748-52 (2004).

Wang, D. et al., "Simultaneous analysis of seven astragalosides in Radix *Astragali* and related preparations by liquid chromatography coupled with electrospray ionization time-of-flight mass spectrometry," *J. Sep. Sci.* 29:2012-22 (2006).

Papadopoulos, G. et al., "Antioxidant effect of natural phenols on olive oil," JAOCS 68(9) (1991) , pp. 669-671.

Office Action dated Oct. 5, 2007 for U.S. Appl. No. 10/563,533.

Office Action dated Sep. 10, 2009 for U.S. Appl. No. 10/562,410.

Office Action dated Nov. 12, 2008 for U.S. Appl. No. 10/562,410.

2 (Cycloastragenol)

4 (Astragaloside IV 16-one)

1 (Astragaloside IV)

3 (Astragenol)

8 (Ginsenoside RH1)

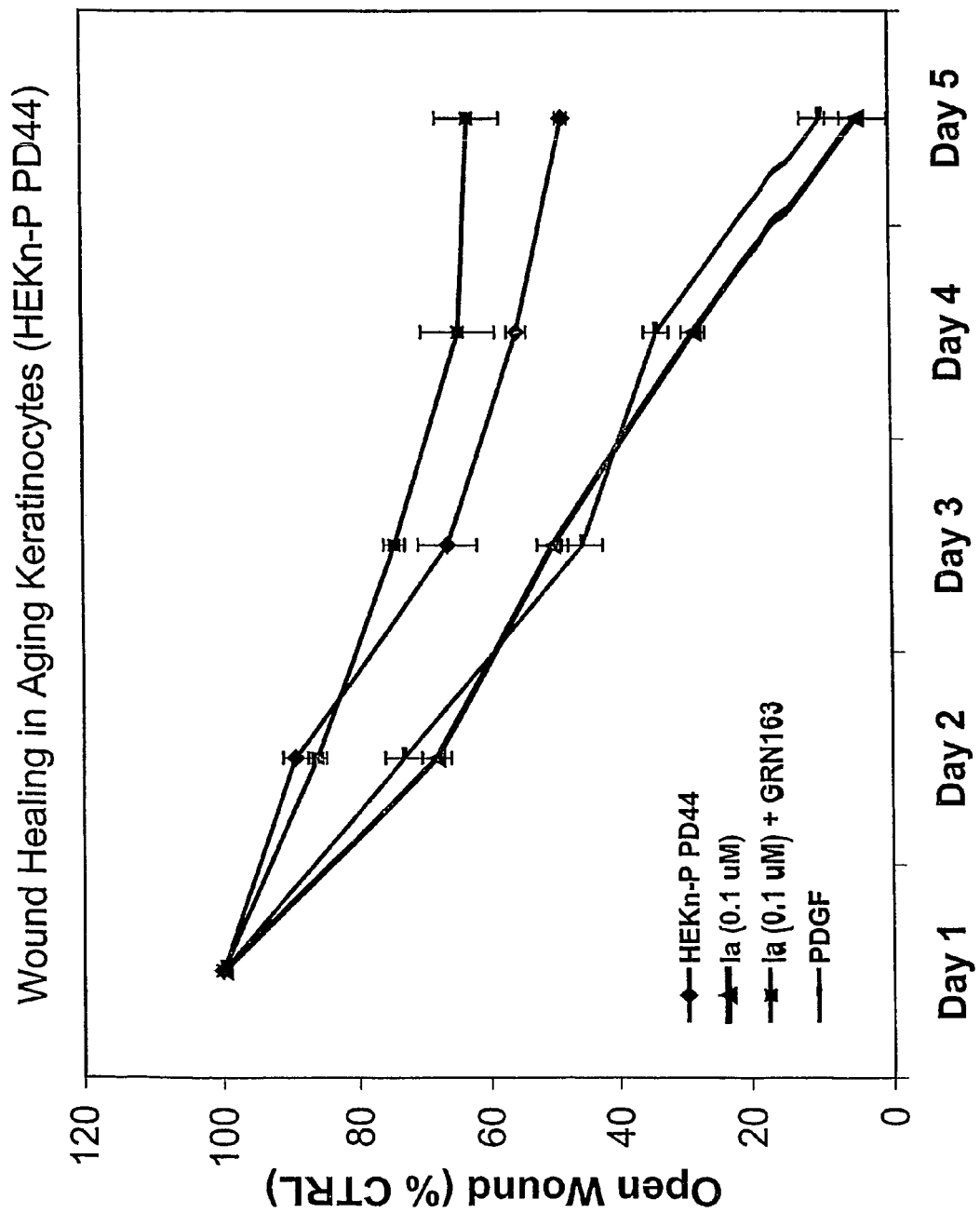

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 1
aatccgtcga gcagagtt                                              18

<210> SEQ ID NO 2
<211> LENGTH: 30
<212> TYPE: DNA
<213> ORGANISM: Artificial Sequence
<220> FEATURE:
<223> OTHER INFORMATION: Synthetic Primer

<400> SEQUENCE: 2
gcgcggctta cccttaccct taccctaacc                                 30

<210> SEQ ID NO 3
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 3
aatccgtcga gcagagttaa aaggccgaga agcgat                          36

<210> SEQ ID NO 4
<211> LENGTH: 18
<212> TYPE: DNA
<213> ORGANISM: Artificial Sequence
<220> FEATURE:
<223> OTHER INFORMATION: Synthetic Primer

<400> SEQUENCE: 4
atcgcttctc ggcctttt                                              18
```

COMPOSITIONS AND METHODS FOR INCREASING TELOMERASE ACTIVITY

This application is a national stage filing of PCT Application Number PCT/US04/20277 filed Jun. 23, 2004, which claims priority to U.S. Provisional Application No. 60/480,988, filed Jun. 23, 2003, both of which are hereby incorporated by reference in their entirety.

FIELD OF THE INVENTION

The present invention relates to methods and compositions for inducing telomerase activity in cells.

BACKGROUND OF THE INVENTION AND REFERENCES

Telomerase

Telomerase is a ribonucleoprotein that catalyzes the addition of telomeric repeats to the ends of telomeres. Telomeres are long stretches of repeated sequences that cap the ends of chromosomes and are believed to stabilize the chromosome. In humans, telomeres are typically 7-10 kb in length and comprise multiple repeats of the sequence-TTAGGG-. Telomerase is not expressed in most adult cells, and telomere length decreases with successive rounds of replication. After a certain number of rounds of replication, the progressive shortening of the telomeres results in the cells entering a telomeric crisis stage, which in turn leads to cellular senescence. Certain diseases are associated with rapid telomeric loss, resulting in premature cell senescence. Expression of the gene encoding the human telomerase protein in human cells has been shown to confer an immortal phenotype, presumably though bypassing the cells' natural senescence pathway. In addition, expression of the telomerase gene in aging cells with short telomeres has been shown to produce an increase in telomere length and restore a phenotype typically associated with younger cells.

Somatic cells, in contrast to tumor cells and certain stem cells, have little or no telomerase activity and stop dividing when the telomeric ends of at least some chromosomes have been shortened to a critical length, leading to programmed cellular senescence (cell death). Since the loss of telomeric repeats in somatic cells, leading to senescence, is augmented by low telomerase activity, induction of telomerase activity, which has the effect of adding arrays of telomeric repeats to telomeres, thereby imparts to mortal somatic cells increased replicative capacity, and impart to senescent cells the ability to proliferate and appropriately exit the cell cycle upon repair of damaged tissue.

Potential therapeutic benefits of increased telomerase activity in somatic cells include, for example, treatment of AIDS, which is characterized by the early senescence of the cytotoxic T lymphocytes (CD8+ cells) which are responsible for killing infected CD4+ cells (see e.g. Dagarag et al., 2003); neuroprotection in Alzheimer's patients (see. e.g. Mattson, 2000); wound healing, and maintenance of explant cells, such as adrenocortical cells (see e.g. Thomas et al., 2000) or bone marrow or stromal/mesenchymal graft cells (see e.g. Simonsen et al., 2002). Full citations of these references appear below.

References discussing these and other characteristics of telomerase include:

Allsopp, R. C. et al., "Telomere shortening is associated with cell division in vitro and in vivo", Exp. Cell Res. 220(1): 194-200 (September 1995).

Allsopp, R. C. et al., "Telomerase is required to slow telomere shortening and extend replicative lifespan of HSC during serial transplantation", Blood (e-publication) Mar. 27, 2003.

Bodnar, A. G. et al., "Extension of life-span by introduction of telomerase into normal human cells" Science 279(5349): 349-52 (Jan. 16, 1998).

Cech, T. R. et al., U.S. Pat. No. 6,093,809 (Jul. 25, 2000).
Cech, T. R. et al., U.S. Pat. No. 6,166,178 (Dec. 26, 2000).
Cech, T. R. et al., U.S. Pat. No. 6,261,836 (July 2001).

Chiu, C. P. et al., "Replicative senescence and cell immortality: the role of telomeres and telomerase" Proc. Soc. Exp. Biol. Med. 214(2):99-106 (February 1997).

Dagarag, M. et al., "Differential impairment of lytic and cytokine functions in senescent human immunodeficiency virus type 1-specific cytotox T lymphocytes", J. Virol. 77(5): 3077-83 (March 2003).

Farwell, D. G. et al., "Genetic and epigenetic changes in human epithelial cells immortalized by telomerase", American Journal of Pathology 156(5): 1537-47 (May 2000).

Fujimoto, R. et al., "Expression of telomerase components in oral keratinocytes and squamous cell carcinomas", Oral Oncology 37(2):132-40 (February 2001).

Funk, Walter D. et al., "Telomerase expression restores dermal integrity to in vitro-aged fibroblasts in a reconstituted skin model", Experimental Cell Research 258(2):270-278 (Aug. 1, 2000).

Hannon, G. J. and Beach, D. H., "Increasing proliferative capacity and preventing replicative senescence by increasing telomerase activity and inhibiting pathways inhibiting cell proliferation", PCT Int. Appl. Pubn. No. WO 2000/031238 (June 2000).

Hannon, G. J. et al., Extension of cellular lifespan using telomerase-activating therapeutic agents", PCT Int. Appl. Pubn. No. WO 99/35243 (July 1999).

Harle-Bachor, C. et al., "Telomerase activity in the regenerative basal layer of the epidermis inhuman skin and in immortal and carcinoma-derived skin keratinocytes", Proc Natl Acad Sci USA 93(13):6476-81 (Jun. 25, 1996).

Harley, C. B. et al., "Telomeres shorten during ageing of human fibroblasts", Nature 345(6274):458-60 (May 31, 1990).

Harley, C. B. et al., "Telomerase, cell immortality, and cancer", Cold Spring Harb. Symp. Quant. Biol. 59:307-15 (1994).

Harley, C. B. et al., "Telomeres and telomerase in aging and cancer", Curr. Opin Genet. Dev. 5(2):249-55 (April 1995).

Harley, C. B. et al., "Telomerase and cancer", Important Adv. Oncol. 57-67 (1996).

Harley, C. B., "Human aging and telomeres", Ciba Found. Symp. 211:129-39 (1997).

Harley, C. B., "Telomerase is not an oncogene", Oncogene 21: 494-502 (2002)

Henderson, S. et al., "In situ analysis of changes in telomere size during replicative aging and cell transformation", J. Cell Biol. 134(1):1-12 (July 1996).

Jiang, X. R. et al., PCT Pubn. No. WO 02/91999.

Jiang, X. R. et al., "Telomerase expression in human somatic cells does not induce changes associated with a transformed phenotype", Nature Genetics 21(1): 111-4 (January 1999).

Kang, M. K. et al., "Replicative senescence of normal human oral keratinocytes is associated with the loss of telomerase activity without shortening of telomeres", Cell Growth & Differentiation 9(1):85-95 (January 1998).

Kim, N. W. et al., "Telomerase activity assays", U.S. Pat. No. 5,629,154 (May 1997).

Lee, K. M. et al., "Immortalization with telomerase of the Nestin-positive cells of the human pancreas", *Biochem Biophys Res Commun* 301(4):1038-44 (Feb. 21, 2003).

Ludwig, A. et al., "Ribozyme cleavage of telomerase mRNA sensitizes breast epithelial cells to inhibitors of topoisomerase", *Cancer Res.*, 61: 3053-3061 (2001).

Mattson, M. P., "Emerging neuroprotective strategies for Alzheimer's disease: dietary restriction, telomerase activation, and stem cell therapy", *Exp Gerontol.* 35(4):489-502 (July 2000).

Morales, C. P. et al., "Absence of cancer-associated changes in human fibroblasts immortalized with telomerase", *Nature Genetics* 21(1): 115-8 (January 1999).

Oh, H. and Schneider, M. D., "The emerging role of telomerase in cardiac muscle cell growth and survival", *J Mol Cell Cardiol* 34(7):717-24 (July 2002).

Simonsen. J. L. et al. "Telomerase expression extends the proliferative life-span and maintains the osteogenic potential of human bone mar-row stromal cells", *Nat Biotechnol* 20(6): 592-6 (June 2002).

Thomas, M., Yang, L., and Hornsby, P. J., "Formation of functional tissue from transplanted adrenocortical cells expressing telomerase reverse transcriptase", *Nat Biotechnol* 18(1):39-42 (January 2000).

Vasa, M. et al., "Nitric oxide activates telomerase and delays endothelial cell senescence", *Circ. Res.* 87(7):540-542 (2000).

Villeponteau, B. et al., U.S. Pat. No. 5,583,016 (December 1996).

West, M. D. et al., "Methods of screening for compounds that derepress or increase telomerase activity", U.S. Pat. No. 6,007,989 (December 1999).

White, M. A., "Assembly of telomerase components and chaperonins and methods, and compositions for inhibiting or stimulating telomerase assembly", PCT Int. Appl. Pubn. No. WO 2000/08135 (February 2000).

Yang, J. et al., "Telomerized human microvasculature is functional in vivo", *Nature Biotechnology (United States)* 19(3):219-24 (March 2001).

Yang, J., et al., "Human endothelial cell life extension by telomerase expression", *J. Biol. Chem.* 274(37):26141-8 (Sep. 10, 1999).

Yudoh, K. et al., "Reconstituting telomerase activity using the telomerase catalytic subunit prevents the telomere shorting and replicative senescence in human osteoblasts", *J. Bone and Mineral Res.* 16(8):1453-1464 (2001).

Methods of increasing telomerase activity therapeutically have been investigated by, for example, Bodnar (1997), White (2000), Hannon et al. (1999; 2000), Franzese et al. (2001), and Yudoh et al. (2001), all cited above. In these reports, telomerase activity is generally increased by overexpression of hTRT, the gene encoding the protein component of human telomerase, or by expression of proteins which mediate assembly of telomerase, e.g. heat shock proteins (White). Franzese et al. reported that Saquinavir, a protease inhibitor prescribed for treatment of HIV infection, increased telomerase activity in peripheral blood mononuclear cells; Vasa et al. described activation of telomerase, and a resulting delay in endothelial senescence, by administration of a nitric oxide (NO) precursor.

Astragalosides and Ginsenosides

Compounds of the astragaloside and ginsenoside families have been reported as having various biological effects. References discussing biological activity of astragalosides and ginsenosides include:

Bedir, E. et al., "Immunostimulatory effects of cycloartane-type triterpene glycosides from *Astragalus* species", *Biol & Pharm Bull* 23(7):834-7 (2000).

Binder, B. et al., "Use of triterpensaponins, such as notoginsenoside R1 (NR1) and/or astragaloside (ASIV) for preparing medicaments", U.S. Pat. No. 5,770,578 (June 1998).

Calzada, L. et al., "Effect of tetracyclic triterpenes (argentatins A, B and D) on the estradiol receptor of hormone-dependent tumors of human breast", *Medical Science Research* 23(12):815-16 (1995).

Chen, X. et al., "Protective effect of ginsenoside Rg1 on dopamin-induced apoptotis in PC12 cells", *Acta Pharmacol Sinica* 22(8):673-678 (2001).

Hashimoto, K. et al., "Skin tissue regeneration promoters comprising ginsenoside Rb1", WO 200192289 (2001); EP 1295893 A1 (2003).

Hong, H.-Y. et al., "Stimulatory effects of ginsenoside-Rg$_1$ on p56$^{lck}$ kinase and cell proliferation in Jurkat T cells", *Korean J. Ginseng Sci.* 19(2): 117-21 (1995).

Huang, Y. et al., "Selected non-timber forest products with medicinal applications from Jilin Province in China", Conference Title: Forest communities in the third millennium: Linking research, business, and policy toward a sustainable non-timber forest product sector; Kenora, Ontario, Canada, 1-4 Oct., 1999; General Technical Report-North Central Research Station, USDA Forest Service (No. NC-217): p. 93-101 (2000).

Kaneko, M. et al., "Accelerated recovery from cyclophosphamide-induced leukopenia in mice administered a Japanese ethical herbal drug, *Hochu-ekki-to*", *Immunopharmacology* 44(3):223-231 (1999).

Kinjo, J. et al., "Anti-herpes virus activity of fabaceous triterpenoidal saponins", *Biological & Pharmaceutical Bulletin* 23(7):887-9 (July 2000).

Khushbaktova, Z. A. et al., "Influence of cycloartanes from plants of the genus *Astragalus* and their synthetic analogs on the contractive function of the myocarbium and the activity of Na, K-ATPase", *Chem. Nat. Compounds* 30(4): 469-473 (1994).

Lee, Y. J. et al., "Ginsenoside-Rg1, one of the major active molecules from *Panax ginseng*, is a functional ligand of glucocorticoid receptor", *Mol Cell Endocrinol* 133(2):135-40 (October 1997).

Liu, P. et al., "Effect of ginsenosides Rb1, Rg1, Rh1 and Re on proliferation of cells in vitro", *Tianraw Chanwzt Yanjiu Yu Kaifa* 8(4):36-41 (1996); CA Abstract No. 1997:400846.

Oda, K. et al., "Adjuvant and haemolytic activities of 47 saponins derived from medicinal and food plants", *Biol. Chem.* 381(1):67-74 (2000).

Pistelli, L., et al., "Antimicrobial and antifungal activity of crude extracts and isolated saponins from *Astragalus verrucosus*", *Fitoterapia* 73(4):336-339 (2002).

Prince, R. L. and Min X., "Compositions and method for treating or preventing osteoporosis", PCT Pubn. No. WO 2001/01996.

Sengupta, S. et al., "Pharmaceutically effective compounds and their use", PCT Pubn. Nos. WO 2002/69980 and WO 2002/07732.

Wang, S. et al., "Promoting effect of ginsenoside Re on the proliferation of murine bone marrow cells", *Baiqiuen Yike Doxue Xuebao* 23(2): 141-142 (1997); CA Abstract No. 1997:570234.

Wang, Y-P. et al., "Effect of astragaloside IV on T, B lymphocyte proliferation and peritoneal macrophage function in mice", *Acta Pharmacologica Sinica* 23(3):263-6 (March 2002).

Yasukawa, K. et al., "Sterol and triterpene derivatives from plants inhibit the effects of a tumor promoter, and sitosterol and betulinic acid inhibit tumor formation in mouse skin two-stage carcinogenesis", *Oncology* 48(1):72-6 (1991).

Yamamoto, M. et al., "The stimulatory effects of ginseng saponins on proliferation and DNA synthesis of human vascular endothelial cells and skin fibroblasts in relation to cytokines or growth factors", *Nissei Byoin Igaku Zasshi* 24(1): 12-13 (1996).

Zhang W. J. et al., "Regulation of the fibrinolytic potential of cultured human umbilical vein endothelial cells: astragaloside IV downregulates plasminogen activator inhibitor-1 and upregulates tissue-type plasminogen activator expression", *Journal of Vascular Research* 34(4):273-80 (July-August 1997).

Zi-Pu, L. and Qian, C., "Effects of astragaloside IV on myocardial calcium transport and cardiac function in ischemic rats", *Acta Pharmacol Sin* 23(10): 898-904 (October 2002).

SUMMARY OF THE INVENTION

The invention described herein is generally related to methods for increasing telomerase activity in cells and compositions for use in such methods. Such methods and compositions may be used on cells in cell culture, i.e. in vitro or ex vivo, or in vivo, such as cells growing in tissues of a subject, including human subjects and non-human animals, particularly non-human mammals.

In particular embodiments, the compositions comprise a compound of formula I, II, or III as described below. Aspects of the invention include formulations of such compounds for use in cosmetic, nutraceutical and pharmaceutical applications, in particular in applications where increasing telomerase activity in cells is shown to be, or expected to be, beneficial. Methods of using the compounds and formulations thereof for such applications are also provided, including methods for applying or administering such formulations after the need for, or advantage of, increasing telomerase activity in cells or tissues has been determined.

The present invention includes, in one aspect, a method of increasing telomerase activity in a cell or tissue. The method comprises contacting the cell or tissue with a formulation of an isolated compound of formula I, formula II, or formula III below. In preferred embodiments, the compound is of formula I or II below. The method may further comprise the preliminary step of identifying a cell or tissue in which an increase in telomerase activity is desired.

In compounds of formula I:

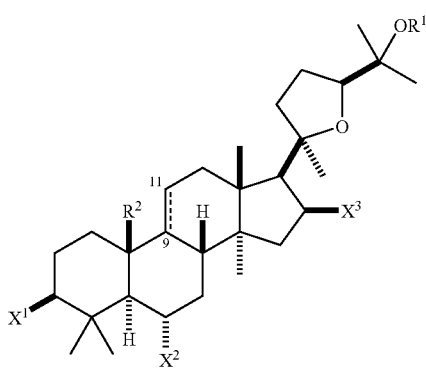

each of $X^1$, $X^2$, and $X^3$ is independently selected from hydroxy, lower alkoxy, lower acyloxy, keto, and a glycoside;

$OR^1$ is selected from hydroxy, lower alkoxy, lower acyloxy, and a glycoside;

wherein any of the hydroxyl groups on said glycoside may be substituted with a further glycoside, lower alkyl, or lower acyl, such that the compound includes a maximum of three glycosides; and $R^2$ is methyl and ═represents a double bond between carbons 9 and 11; or, in preferred embodiments, $R^2$ forms, together with carbon 9, a fused cyclopropyl ring, and ═represents a single bond between carbons 9 and 11.

Preferably, the compound includes zero, one, or two, more preferably zero or two, glycosides, none of which is substituted with a further glycoside. Preferably, glycosides are of the D (naturally occurring) configuration.

In selected embodiments of formula I, each of $X^1$ and $X^2$ is independently selected from hydroxy, lower alkoxy, lower acyloxy, and a glycoside, and $X^3$ is selected from hydroxy, lower alkoxy, lower acyloxy, keto, and a glycoside. In further embodiments, $X^1$ is OH or a glycoside, each of $X^2$ and $OR^1$ is independently OH or a glycoside, and $X^3$ is OH or keto. Exemplary compounds of formula I include astragaloside IV, cycloastragenol, astragenol, astragaloside IV 16-one, cycloastragenol 6-β-D-glucopyranoside, and cycloastragenol 3-β-D-xylopyranoside. In selected embodiments, the compound is selected from astragaloside IV, cycloastragenol, astragenol, and astragaloside IV 16-one. In one embodiment, the compound is astragaloside IV.

In compounds of formula II:

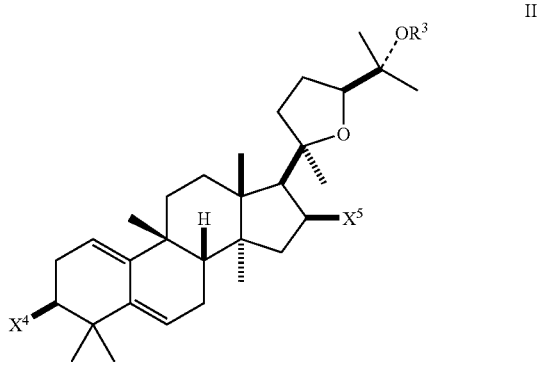

each of $X^4$ and $X^5$ is independently selected from hydroxy, lower alkoxy, lower acyloxy, keto, and a glycoside, and $OR^3$ is selected from hydroxy, lower alkoxy, lower acyloxy, and a glycoside, wherein any of the hydroxyl groups on said glycoside may be substituted with a further glycoside, lower alkyl, or lower acyl, such that the compound includes a maximum of three glycosides.

Preferably, the compound includes zero, one, or two glycosides, none of which is substituted with a further glycoside; glycosides are preferably of the D configuration.

In selected embodiments of formula II, each of $X^4$ and $OR^3$ is selected from hydroxy, lower alkoxy, lower acyloxy, and a glycoside, and $X^5$ is selected from hydroxy, lower alkoxy, lower acyloxy, and keto (═O). In further embodiments, $X^4$ is OH or a glycoside, and each of $X^5$ and $OR^3$ is OH. In one embodiment, $X^4$ is OH.

In compounds of formula III:

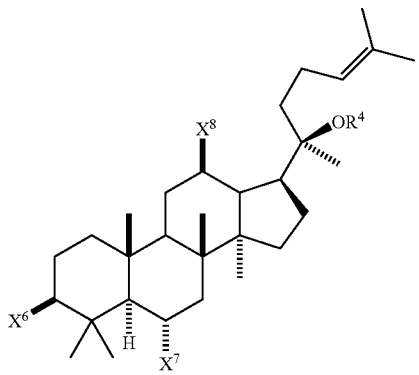

each of $X^6$, $X^7$, and $X^8$ is independently selected from hydroxy, lower alkoxy, lower acyloxy, keto, and a glycoside, and $OR^4$ is selected from hydroxy, lower alkoxy, lower acyloxy, and a glycoside, wherein any of the hydroxyl groups on said glycoside may be substituted with a further glycoside, lower alkyl, or lower acyl, such that the compound includes a maximum of three glycosides.

Preferably, the compound includes zero, one, or two glycosides, none of which is substituted with a further glycoside; glycosides are preferably of the D configuration.

In selected embodiments of formula III, each of $X^6$, $X^7$, $X^8$ and $OR^4$ is independently selected from hydroxy, lower alkoxy, lower acyloxy, and a glycoside, and is preferably selected from hydroxy and a glycoside. In further embodiments, each of $X^8$ and $OR^4$ is OH, and each of $X^6$ and $X^7$ is independently selected from hydroxyl and a glycoside. In still further embodiments, each of $OR^4$, $X^6$ and $X^8$ is OH, and $X^7$ is a glycoside. An exemplary compound of formula III is ginsenoside RH1.

A preferred compound of formula I, II or III above, when formulated in a solvent at a concentration of 1 μg/ml or less, is effective to produce a level of telomerase activity in keratinocytes or fibroblasts, as measured in a TRAP assay, at least 50% greater than the level in said cells treated with said solvent, as measured in a TRAP assay as described herein. In further preferred embodiments, the compound is effective to produce a level of telomerase activity in keratinocytes or fibroblasts, as measured in a TRAP assay, at least 100% greater than the level in said cells treated with said solvent, as measured in a TRAP assay as described herein.

Exemplary compounds of formulas I-III include those depicted in FIG. 1 and designated herein as 1 (astragaloside IV), 2 (cycloastragenol), 3 (astragenol), 4 (astragaloside IV 16-one), 5 (2OR,24S-epoxy-3β,16β,25-trihydroxy-9β-methyl-19-norlanost-1,5-diene), 6 (cycloastragenol 6-β-D-glucopyranoside), 7 (cycloastragenol 3-β-D-xylopyranoside), and 8 (ginsenoside RH1). In selected embodiments, the compound is selected from those designated herein as 1 (astragaloside IV), 2 (cycloastragenol), 3 (astragenol), 4 (astragaloside IV 16-one), 5 (2OR,24S-epoxy-3β,16β,25-trihydroxy-9β-methyl-19-norlanost-1,5-diene), 6 (cycloastragenol 6-β-D-glucopyranoside), and 7 (cycloastragenol 3-β-D-xylopyranoside). In further embodiments, the compound is selected from those designated herein as 1, 2, 3, 4, and 5. In one embodiment, the compound is astragaloside IV (1) or cycloastragenol (2).

The method of contacting a formulation of an isolated compound of formula I, II, or III with a cell or tissue may comprise, prior to said contacting, identifying a cell or tissue in which an increase in telomerase activity is desired. Benefits to be realized by increasing telomerase activity in a cell or tissue include, for example, enhancement of the replicative capacity and/or life span of said cell or cells within said tissue.

The method may include diagnosing a condition in a subject such that increasing telomerase activity in the cells or tissue of the subject is desired, and administering the formulation to the subject. The subject is preferably a mammalian subject, such as a human subject or patient. Such conditions may include, for example, HIV infection, various degenerative diseases, such as neurodegenerative disease, degenerative disease of the bones or joints, macular degeneration, atherosclerosis, and anemia. Such conditions also include wounds or other acute or chronic conditions of the epidermis, such as, for example, a burn, an abrasion, an incision, a graft site, a lesion caused by an infectious agent, a chronic venous ulcer, a diabetic ulcer, a compression ulcer, a pressure sores, a mucosal ulcer, and keloid formation.

Accordingly, the invention provides methods of treating a condition in a patient, such as those noted above, by increasing telomerase activity in cells or tissue of the patient, the method comprising administering to a patient in need of such treatment, a formulation of an isolated compound of formula I, of formula II, or of formula III, as defined above. The compositions may be administered by various routes, for example, orally, topically, or parenterally.

The invention further provides a method of diagnosing in a subject a disease state subject to treatment by increasing telomerase activity in a cell or tissue of the subject, and administering a compound of formula I, II or III as described above, preferably a compound of formula I or II, in a pharmaceutical vehicle, to the subject in need of such treatment.

In a further aspect, the invention provides a method of treating an acute or chronic condition of the epidermis, comprising contacting epidermal cells with a topical formulation of an isolated compound of formula I, of formula II, or of formula III, as defined above. In preferred embodiments, the compound is of formula I or formula II. In further embodiments, the compound is selected from astragaloside IV, cycloastragenol, astragenol, astragaloside IV 16-one, cycloastragenol 6-β-D-glucopyranoside, cycloastragenol 3-β-D-xylopyranoside, and 2OR,24S-epoxy-3β,16β,25-trihydroxy-9β-methyl-19-norlanost-1,5-diene (designated herein as 5).

The cells with which the formulation is contacted may also include explant cells which are contacted ex vivo, e.g. for cell-based therapies, or other cells in culture. Accordingly, the invention provides a method of enhancing replicative capacity of cells in vitro or ex vivo, comprising contacting said cells with an effective amount of a composition comprising a compound of formula I, of formula II, or of formula III, as defined above, including selected embodiments of the compounds as defined above. In preferred embodiments, the compound is of formula I or formula II, including selected embodiments of the compounds as defined above. In general, the cells are non-transformed mammalian cells; in selected embodiments, the cells are stem cells, such as bone marrow stem cells, bone marrow stromal cells, young or early passage dermal fibroblasts, islet precursor cells, neurosphere cells, adrenocortical cells, muscle satellite cells, osteoblasts, retinal pigmented epithelial cells, and HIV-restricted $CD8^+$ cells.

In a related aspect, the invention provides a pharmaceutical composition comprising, in a pharmaceutically acceptable vehicle, a compound of formula I as depicted above, where:

each of $X^1$ and $X^2$ is independently selected from hydroxy, lower alkoxy, lower acyloxy, keto, and a glycoside;

$X_3$ is keto;

$OR^1$ is selected from hydroxy, lower alkoxy, lower acyloxy, and a glycoside;

wherein any of the hydroxyl groups on said glycoside may be substituted with a further glycoside, lower alkyl, or lower acyl, such that the compound includes a maximum of three glycosides; and $R^2$ is methyl and ═represents a double bond between carbons 9 and 11; or, in preferred embodiments, $R^2$ forms, together with carbon 9, a fused cyclopropyl ring, and ═represents a single bond between carbons 9 and 11.

Preferably, the compound includes zero, one, or two glycosides, none of which is substituted with a further glycoside, and glycosides are of the D configuration.

In selected embodiments of the composition, $X^1$ is OH or a glycoside, and each of $X^2$ and $OR^1$ is independently OH or a glycoside. In one embodiment, the compound is astragaloside IV 16-one (designated herein as 4).

Alternatively, the composition comprises, in a pharmaceutically acceptable vehicle, a compound of formula I as depicted above, where:

one of $X^1$ and $X^2$ is selected from hydroxy, lower alkoxy, lower acyloxy, and keto, and the other is a glycoside; and each of $X_3$ and $OR^1$ is independently selected from hydroxy, lower alkoxy, lower acyloxy, and a glycoside;

wherein any of the hydroxyl groups on said glycoside may be substituted with a further glycoside, lower alkyl, or lower acyl, such that the compound includes a maximum of three glycosides; and $R^2$ is methyl and ═represents a double bond between carbons 9 and 11; or, in preferred embodiments, $R^2$ forms, together with carbon 9, a fused cyclopropyl ring, and ═represents a single bond between carbons 9 and 11.

Preferably, the compound includes one glycoside, which is not substituted with a further glycoside, and which is of the D configuration. In one embodiment, the compound is selected from cycloastragenol 6-β-D-glucopyranoside (designated herein as 6) and cycloastragenol 3-β-D-xylopyranoside (designated herein as 7).

Alternatively, the pharmaceutical composition comprises, in a pharmaceutically acceptable vehicle, a compound of formula II as defined above. Selected embodiments of the compound are also defined above. In one embodiment, the compound is that designated herein as 5.

The invention also provides compounds of formula II as defined above, including selected embodiments as defined above. In one embodiment, the compound is that designated herein as 5.

In a related aspect, the invention provides a topical pharmaceutical formulation of a an isolated compound of formula I, of formula II, or of formula III, as defined above. Selected embodiments of the compounds are also defined above. In preferred embodiments, the compound is of formula I or formula II. In further embodiments, the compound is selected from astragaloside IV, cycloastragenol, astragenol, astragaloside IV 16-one, cycloastragenol 6-β-D-glucopyranoside, cycloastragenol 3-β-D-xylopyranoside, and 2OR,24S-epoxy-3β,16β,25-trihydroxy-9β-methyl-19-norlanost-1,5-diene (designated herein as 5). The topical formulation typically comprises one or more components selected from the group consisting of an emulsifier, a thickener, and a skin emollient. Such compositions may be used for treatment of wounds or other acute or chronic conditions of the epidermis.

In another related aspect, the invention provides nutraceutical compositions comprising a nutraceutical formulation of an isolated compound of formula I, of formula II, or of formula III, as defined above. Selected embodiments of the compounds are also defined above. In preferred embodiments, the compound is of formula I or formula II, including selected embodiments as defined above. In further embodiments, the compound is selected from astragaloside IV, cycloastragenol, astragenol, astragaloside IV 16-one, cycloastragenol 6-β-D-glucopyranoside, cycloastragenol 3-β-D-xylopyranoside, and 2OR,24S-epoxy-3β,16β,25-trihydroxy-9β-methyl-19-norlanost-1,5-diene (designated herein as 5). In further embodiments, the nutraceutical formulation comprises, in addition to the isolated compound of formula I, II or III, a nutraceutical herbal extract, which may be an extract of *Astragalus membranaceus*.

An isolated compound of formula I, II, or III, as defined above, including selected embodiments as described above, can also be used for the manufacture of a medicament for treating a disease subject to treatment by increasing telomerase activity in a cell or tissue. Examples of such diseases are discussed in more detail below. Similarly, an isolated compound of formula I, II, or III, as defined above, including selected embodiments as described above, can also be used for the manufacture of a medicament for treatment of a chronic or acute condition of the epidermis. In preferred embodiments of such uses, the isolated compound is of formula I or formula II, including selected embodiments of formula I or formula II as described above.

Also provided is a method of selecting a compound effective to increase telomerase activity in a cell. In accordance with this method, a derivative of a compound of formula I, formula II, formula III, as defined above, is tested for its ability to increase telomerase activity in keratinocytes or fibroblasts, as measured by a TRAP assay as described herein. The derivative is selected if, when formulated in a solvent at a concentration of 1 μg/ml or less, is effective to produce a level of telomerase activity in keratinocytes or fibroblasts, as measured in a TRAP assay, at least 50% greater, and preferably at least 100% greater, than that measured in said cells treated with said solvent. The derivative can then be formulated with a topical, pharmaceutical or nutraceutical vehicle.

Also provided, in a related aspect, is a method of selecting an agent for treatment of acute or chronic conditions of the epidermis. In accordance with this method, a derivative of a compound of formula I, formula II, formula III, as defined above, is tested for wound healing activity in keratinocytes or fibroblasts, in a scratch assay as described herein. The derivative is selected if it has a wound healing activity as measured in a scratch assay, at a concentration of 1 μg/ml, at least 50% greater than that of a solvent control, preferably at least 100% greater than that of a solvent control. The derivative can then be formulated with a topical vehicle.

These and other objects and features of the invention will become more fully apparent when the following detailed description of the invention is read in conjunction with the accompanying drawings.

BRIEF DESCRIPTION OF THE DRAWINGS

FIG. 7 is a graph showing wound healing activity of 1 (astragaloside IV) in aging neonatal keratinocytes, in the presence and absence of the telomerase inhibitor GRN163, and in comparison with ~2 nM PDGF (platelet derived growth factor).

DETAILED DESCRIPTION OF THE INVENTION

I. Definitions

Figure 1B:
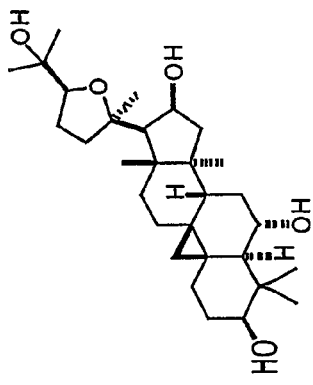
FIGS. 1A-H show the structures of exemplary compounds for use in the methods and compositions described herein.
Figure 1D:
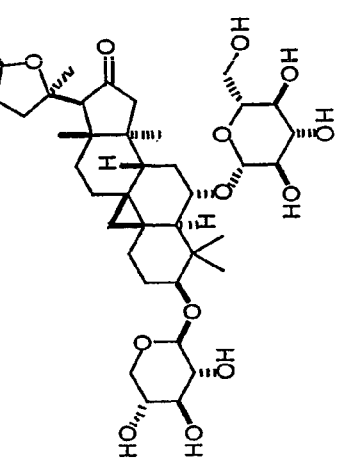
Figure 1A:
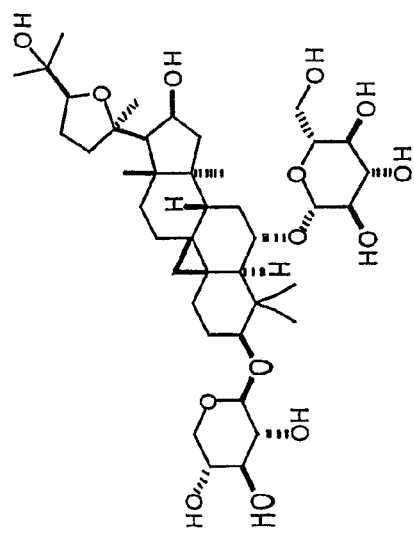
Figure 1C:
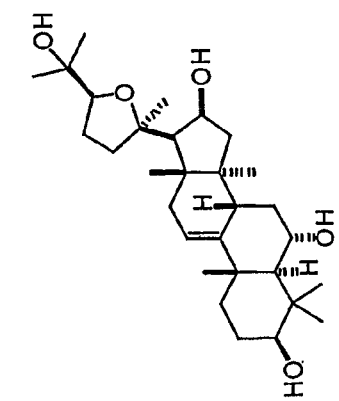
Figure 1F:
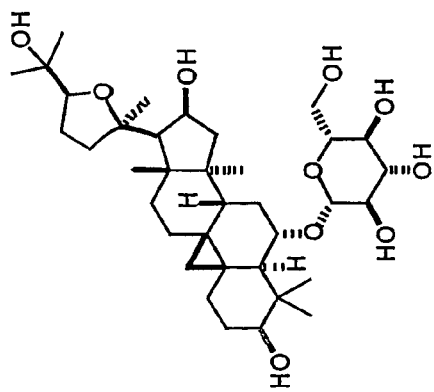
Figure 1H:
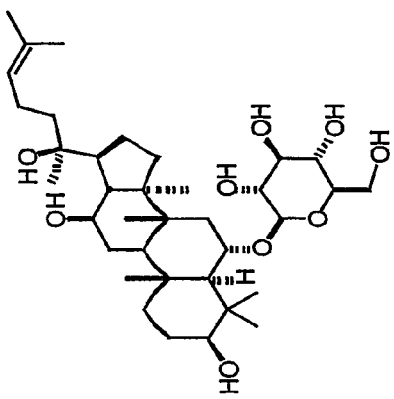
Figure 1E:
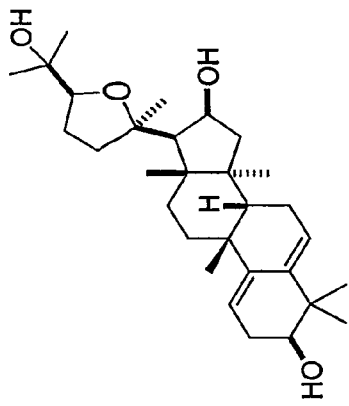
Figure 1G:
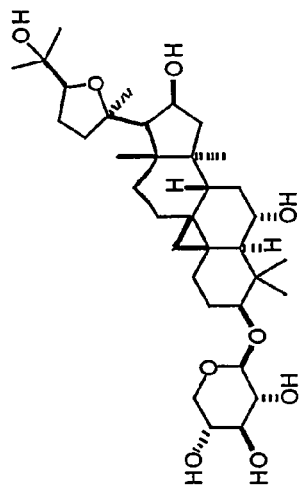

The following terms, as used herein, have the meanings given below, unless indicated otherwise.

A general carbon atom numbering scheme used for nomenclature of compounds described herein is shown below. (Note that compounds of structure II lack the 19 carbon, and compounds of structure III lack the 18 carbon shown in this scheme. Accordingly, the numbering scheme is not intended to limit the compositions of the invention.)

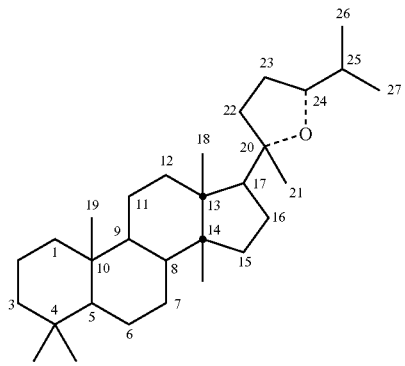

"Alkyl" refers to a fully saturated acyclic monovalent radical containing carbon and hydrogen, which may be branched or linear. Examples of alkyl groups are methyl, ethyl, n-butyl, t-butyl, n-heptyl, and isopropyl. "Alkoxy" refers to a group of the form OR, where R is alkyl as defined above. "Acyloxy" refers to a group of the form —OC(=O)R, where R is alkyl as defined above. Accordingly, "acyl" refers to the group —C(=O)R.

"Lower alkyl" (or lower alkoxy, or lower acyloxy) refers to such a group having one to six carbon atoms; in selected embodiments, such groups include one to four carbon atoms, one or two carbon atoms, or one carbon atom (i.e. methyl, methoxy, acetyloxy).

"Stem cells" refer to relatively undifferentiated cells of a common lineage that retain the ability to divide and cycle throughout postnatal life, to provide cells that can differentiate further and become specialized (e.g. stem cells in basal layers of skin or in haematopoetic tissue, such as primitive cells in the bone marrow from which all the various types of blood cell are derived).

By "effective to increase telomerase activity in a cell", with reference to a compound, is meant that a composition containing the compound at a concentration of 1 μg/ml or less is effective to produce a level of telomerase activity in a keratinocyte or fibroblast cell, as measured in a TRAP assay as described herein, which is greater, by a factor of at least 1.5 (i.e. at least 50% greater), than the level produced by a similar formulation not containing the compound, as measured in a TRAP assay. In preferred embodiments, the compound is effective, at a concentration of 1 μg/ml or less, to produce a level of telomerase activity in such a cell, as measured in a TRAP assay as described herein, which is greater by a factor of at least 2 (i.e. at least 100% greater) than the level produced by a similar formulation not containing the compound.

In reference to administration of a compound to a patient, an "effective amount" refers to an amount effective to increase telomerase activity in the cells or tissue of the patient, such that a desired therapeutic result is achieved. In reference to treatment of cells in vitro or ex vivo, an "effective amount" refers to an amount effective to increase telomerase activity in the cells, thereby increasing the replicative capacity and/or life span of the cells.

In concentrations expressed herein as % (w/v), 100% (w/v) corresponds to 1 g solute/ml solvent. For example, 0.1% (w/v)=1 mg/ml.

A "formulation of an isolated compound" refers to a formulation prepared by combining the isolated compound with one or more other ingredients (which may be active or inactive ingredients) to produce the formulation. Where the compound has been directly purified from a natural source, the phrase "isolated compound" requires that the compound (prior to the formulation) has been purified not less than 100-fold compared to the purity of the compound in the natural source. Where the compound is not purified directly from a natural source, the phrase "isolated compound" refers to a compound that (prior to the formulation) has been produced by a process involving one or more chemical synthesis steps, resulting in a preparation of the compound that is of not less than 5% (w/w) purity.

II. Methods and Compositions for Increasing Telomerase Activity

In accordance with the present invention, compositions and methods are provided for increasing telomerase activity in a cell. In accordance with the method, a cell or tissue is contacted with a formulation of an isolated compound of formula I, II or III as disclosed herein, in an amount effective to increase telomerase activity in the cell or tissue, relative to the level of telomerase activity in the cell or tissue in the absence of the compound. The method may also include a preliminary step of identifying a cell or tissue in which an increase in telomerase activity is desired.

In one embodiment, the compound is represented by formula I:

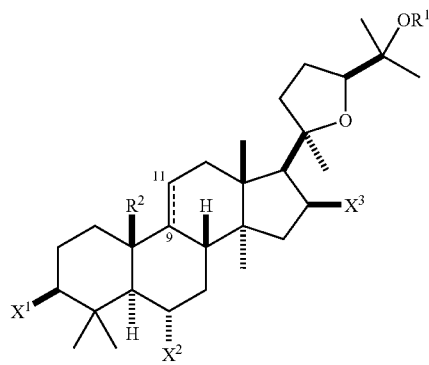

In formula I, each of $X^1$, $X^2$, and $X^3$ is independently selected from hydroxy, lower alkoxy, lower acyloxy, keto, and a glycoside, and the group $OR^1$ is selected from hydroxy, lower alkoxy, lower acyloxy, and a glycoside. In selected embodiments, each of $X^1$ and $X^2$ is independently selected from hydroxy, lower alkoxy, lower acyloxy, and a glycoside.

In selected embodiments of formula I, $R^2$ is methyl and ═══ represents a double bond between carbons 9 and 11, as depicted. In other embodiments, $R^2$ forms, together with carbon 9, a fused cyclopropyl ring; and ═══ represents a single bond between carbons 9 and 11, as shown for example, in compound 1 (see FIG. 1).

By a "glycoside", as used herein in reference to any of the subject compounds of formulas I, II, or III (or derivatives thereof), is meant one of the known glycosides (i.e. riboside, arabinoside, xyloside, lyxoside, altroside, glucoside, mannoside, guloside, idoside, galactoside, and taloside). The glycoside is typically in the six-membered ring (pyranose) form, e.g., glucopyranoside or mannopyranoside. In selected embodiments, the glycoside is a D-glycoside; that is, it has the configuration found in naturally occurring monosaccharides. Specific examples include D-ribopyranoside, D-arabinopyranoside, D-xylopyranoside, D-glucopyranoside, mannopyranoside, and D-galactopyranoside. Preferred glycosides include D-glucopyanoside and D-xylopyranoside. In further embodiments, the linkage is of the β configuration; e.g. β-D-glucopyranoside.

Any of the free hydroxyl groups on a glycoside ring present in the subject compounds of formulas I, II or III (or derivatives thereof) may be further substituted with a further glycoside, lower alkyl, or lower acyl, e.g. methoxy or acetyloxy. Preferably, at most one such hydroxyl group is substituted with a further glycoside. More preferably, no such hydroxyl group is substituted with a further glycoside; i.e., the substitution is lower acyl, such as acetyl, or lower alkyl, such as methyl. In one embodiment, all of the hydroxyl groups on the glycoside(s) are unsubstituted.

Preferably, a subject compound of formula I, II, or III (or a derivative thereof) includes a maximum of three glycosides, more preferably a maximum of two glycosides. In selected embodiments, the compound includes zero, one, or two glycosides, none of which is substituted with a further glycoside. In further selected embodiments, particularly with respect to formula I, the compound includes zero or two glycosides, none of which is substituted with a further glycoside.

In selected embodiments of formula I, each of $X^1$ and $X^2$ is independently selected from hydroxy, lower alkoxy, lower acyloxy, glucopyranoside, and xylopyranoside, and $X^3$ is selected from hydroxy, lower alkoxy, lower acyloxy, keto, glucopyranoside, and xylopyranoside, preferably from hydroxy, lower alkoxy, lower acyloxy, and keto.

In further embodiments of formula I, $X^1$ is selected from hydroxy, lower alkoxy, lower acyloxy, and β-D-xylopyranoside; $X^2$ is selected from hydroxy, lower alkoxy, lower acyloxy, and β-D-glucopyranoside; $X^3$ is selected from hydroxy, lower alkoxy, lower acyloxy, and keto (═O); and $OR^1$ is selected from hydroxy, lower alkoxy, lower acyloxy, and β-D-glucopyranoside.

In further selected embodiments of formula I, $X^1$ is OH or a glycoside, each of $X^2$ and $OR^1$ is independently OH or a glycoside, and $X^3$ is OH or keto. In further embodiments, each of $X^1$ and $X^2$ is OH or a glycoside, $OR^1$ is OH, and $X^3$ is OH. In still further embodiments, $X^1$ is β-D-xylopyranoside, $X^2$ is β-D-glucopyranoside, $OR^1$ is OH, and $X^3$ is OH. In another embodiment, each of $X^1$, $X^2$, $X^3$ and $OR^1$ is OH.

For each of these described embodiments, further embodiments include compounds in which $R^2$ is methyl and ═══ represents a double bond, and other embodiments, generally preferred, include compounds in which $R^2$ forms, with carbon 9, a fused cyclopropyl ring.

Exemplary compounds of structure I for use in the methods of the invention include those shown in FIG. 1, and designated herein as 1 (astragaloside IV), 2 (cycloastragenol), 3 (astragenol), 4 (astragaloside IV 16-one), 6 (cycloastragenol 6-β-D-glucopyranoside), and 7 (cycloastragenol 3-β-D-xylopyranoside).

Other compounds having the backbone structure of cycloastragenol (2) substituted with a 3-β-D-glycopyranoside are also considered for use in the methods of the invention. Preferably, the compound includes a total of one or two glycosides, attached to separate carbons of the backbone structure (i.e. one glycoside is not attached to a further glycoside). Examples include the naturally occurring compounds astragalosides A, 1, 2, and 7, as well as the astraverrucins I and II (which can be isolated from *Astragalus verrucosus*).

The invention also provides pharmaceutical compositions comprising one or more compounds of formula I, wherein one of $X^1$ and $X^2$ is selected from hydroxy, lower alkoxy, lower acyloxy, and keto, and the other is a glycoside. In further embodiments, the compounds are selected from those designated 6 and 7. In other embodiments, the pharmaceutical composition includes a compound of formula I in which $X^3$ is keto; in one embodiment, the compound is the compound designated as 4.

In another aspect, the invention provides pharmaceutical compositions comprising compounds represented by formula II.

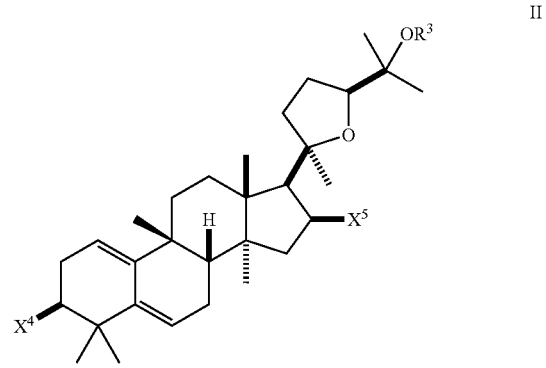

II

In formula II, each of $X^4$ and $X^5$ is independently selected from hydroxy, lower alkoxy, lower acyloxy, keto, and a glycoside, and $OR^3$ is selected from hydroxy, lower alkoxy, lower acyloxy, and a glycoside; where "glycoside" and its various embodiments are as described above. As noted above, the compound includes a maximum of three glycosides, more preferably a maximum of two glycosides. In selected embodiments, the compound includes zero, one, or two glycosides, none of which is substituted with a further glycoside.

In selected embodiments of formula I, $X^4$ is selected from hydroxy, lower alkoxy, lower acyloxy, and a glycoside. In further embodiments, each of $X^4$, $X^5$, and $OR^3$ is independently selected from hydroxy, lower alkoxy, lower acyloxy, glucopyranoside, and xylopyranoside.

In further embodiments of formula II, each of $X^4$ and $OR^3$ is selected from hydroxy, lower alkoxy, lower acyloxy, and a glycoside, preferably D-xylopyranoside or D-glucopyranoside, and $X^5$ is selected from hydroxy, lower alkoxy, lower acyloxy, and keto (═O). Preferably, in these embodiments, $OR^3$ is selected from hydroxy, lower alkoxy, and lower acyloxy, and is more preferably hydroxy.

In further embodiments of formula II, each of $X^4$, $X^5$, and $OR^3$ is independently OH or a glycoside, e.g. D-xylopyranoside or D-glucopyranoside. In still further embodiments, $X^4$ is OH or a glycoside, and each of $X^5$ and $OR^3$ is OH. In one embodiment, each of $X^4$, $X^5$, and $OR^3$ is OH. This compound (formally named 20R,24S-epoxy-3β,16β,25-trihydroxy-9β-methyl-19-norlanost-1,5-diene) is designated herein as 5.

The invention also provides compounds of formula II, above, where each of $X^4$ and $X^5$ is independently selected from hydroxy, lower alkoxy, lower acyloxy, keto, and a glycoside, and $OR^3$ is selected from hydroxy, lower alkoxy, lower acyloxy, and a glycoside, wherein any of the hydroxyl groups on said glycoside may be substituted with a further glycoside, lower alkyl, or lower acyl. In selected embodiments, the compound includes zero, one, or two glycosides. Preferably, each said glycoside, when present, is of the D configuration. In further embodiments, each of $X^4$ and $OR^3$ is selected from hydroxy, lower alkoxy, lower acyloxy, and a glycoside, and $X^5$ is selected from hydroxy, lower alkoxy, lower acyloxy, and keto (=O). In still further embodiments, $X^4$ is OH or a glycoside, and each of $X^5$ and $OR^3$ is OH. In one embodiment, each of $X^4$, $X^5$, and $OR^3$ is OH; i.e. the compound designated herein as 5.

In a further aspect, the invention provides a method of increasing telomerase in a cell or tissue, by contacting the cell or tissue with a formulation of an isolated compound of formula III. Again, the method may include the step of identifying a cell or tissue in which an increase in telomerase activity is desired.

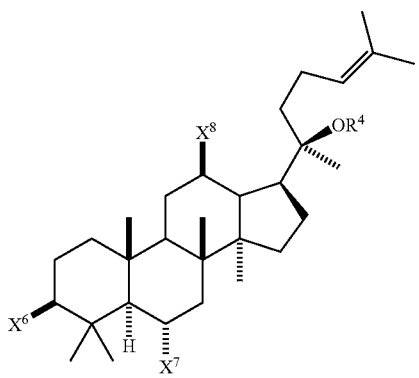

III

In formula III, each of $X^6$, $X^7$, $X^8$ and $OR^4$ is independently selected from hydroxy, lower alkoxy, lower acyloxy, keto, and a glycoside, where "glycoside" and its embodiments are as defined above. Preferably, the compound includes a maximum of two glycosides, more preferably a maximum of one glycoside, none of which is substituted with a further glycoside. Preferred glycosides include D-glucopyranoside and D-xylopyranoside.

In selected embodiments of structure III, each of $X^6$, $X^7$, $X^8$ and $OR^4$ is independently selected from hydroxy, lower alkoxy, lower acyloxy, and a glycoside, and is preferably selected from hydroxy and a glycoside.

In further embodiments of structure III, each of $X^8$ and $OR^4$ is OH, and each of $X^6$ and $X^7$ is independently selected from hydroxyl and a glycoside, e.g. β-D-glucopyranoside. In further embodiments, $OR^4$ is OH. Preferably, each of $X^6$ and $X^8$ is also OH, and $X^7$ is a glycoside. An exemplary compound of structure III is ginsenoside RH1, designated herein as 8.

III. Sources and Syntheses of Compounds of Formulas I-III

The compounds of formulas I, II and III can generally be isolated or synthesized from naturally occurring materials. For example, astragalosides I-VII can be isolated from *Astragalus menmbranaceus* root, as described, for example, in A. Kadota et al., JP Kokai No. 62012791 A2 (1987). As reported therein, the root tissue (8 kg), which is commercially available from various sources of beneficial herbs, is refluxed with MeOH, and the concentrated extract (200 g) is redissolved in MeOH and fractionated by column chromatography on silica gel, using $CHCl_3$/MeOH/$H_2O$ mixtures as eluants. Each fraction is worked up by reverse chromatography on silica gel, using similar solvent mixtures, to give the following approximate quantities of isolated compounds: acetylastragaloside I (0.2 g), astragaloside I (3.5 g), isoastragaloside I (0.3 g), astragaloside II (2.3 g), astragaloside III (1.0 g), astragaloside IV (0.8 g), astragaloside V (0.1 g), astragaloside VI (0.3 g), and astragaloside VII (0.1 g). See also Kitagawa et al., *Chem. Pharm. Bull.* 31(2):698-708 (1983b).

Astragaloside IV (designated herein as 1) was also obtained by the present authors from Ai Chunmei, Chengdu 610041, P.R. China.

Cycloastragenol (2) can be prepared by treatment of astragaloside IV (1) with methanolic HCl, followed by neutralization, standard workup, and purification by chromatography, as described in the Experimental section below (Example 1). Cycloastragenol can also be obtained by oxidative degradation (treatment with oxygen and elemental sodium) of a butanol extract of *Astragalus membranaceus*, as described by P-H Wang et al., *J. Chinese Chem. Soc.* 49:103-6 (2002). Astragenol (3) and cycloastragenol (2) can also be obtained according to the procedure of Kitagawa et al., *Chem. Pharm. Bull.* 31(2):689-697 (1983a).

The compounds designated herein as 6 (cycloastragenol 6-β-D-glucopyranoside) and 7 (cycloastragenol 3-β-D-xylopyranoside) were obtained by refluxing a solution of astragaloside IV (1) and sulfuric acid in methanol, followed by standard workup and silica gel chromatography, as described in the Experimental section below (Example 2). Also obtained were the rearrangement product 5 and the aglycone, i.e. cycloastragenol (2).

The 16-keto compound 4 was prepared by acetylation of the glycoside hydroxyl groups of astragaloside IV, followed by pyridinium chlorochromate oxidation of the 16-hydroxyl, and restoration of the glycoside hydroxyls by treatment with sodium borohydride (see Kitagawa et al., 1983b, cited above).

Preparation of the Various Embodiments of Formulas I-III, e.g. Compounds Having varying degrees of alkylation or acylation, or keto groups, can be prepared according to known methods of organic synthesis, using naturally occurring and/or commercially available starting materials such as cycloastragenol, astragenol, the astragalosides or astraverrucins, or panaxatriol, with separation of products as needed. Several examples are given in the Experimental section below. For example, the less sterically hindered 3-, 6-, and/or 16-hydroxyl groups can generally be selectively modified, e.g. by acylation. If desired, the unreacted hydroxyl groups can then be separately modified, e.g. by alkylation, followed by optional removal of the acyl groups. Compounds of formula I having a fused cyclopropyl ring (e.g. cycloastragenols) can be converted to compounds having a 19-methyl group and 9-11 double bond (e.g. astragenols) by sulfuric acid treatment. This reaction may be accompanied by deglycosylation, as shown in the reactions of Examples 9B and 10B, below.

IV. Determination of Biological Activity

A. TRAP Assay Protocol

The ability of a compound to increase telomerase activity in a cell can be determined using the TRAP (Telomeric Repeat Amplification Protocol) assay, which is known in the art (e.g. Kim et al., U.S. Pat. No. 5,629,154; Harley et al., U.S. Pat. No. 5,891,639). As used herein, "telomerase activity as measured in a TRAP assay" refers to telomerase activity as measured in keratinocytes or fibroblasts according to the following protocol. The activity is typically compared to the activity similarly measured in a control assay of such cells (e.g., a telomerase activity 50% greater than observed in a solvent control).

Cell lines suitable for use in the assay, preferably normal human fibroblasts (NHF) or normal human keratinocytes (NHK), can be obtained from commercial sources, such as Cascade Biologics, Portland, Oreg. or 4C Biotech, Seneffe, Belgium, or from the ATCC (American Type Culture Collection). ATCC normal human fibroblast cell lines, which can be located on the ATCC web site, include, for example, CCL135, CCL137, and CCL151.

Cells are plated at approx. 5000 cells/well, in growth medium (e.g. Epi-Life Medium+Keratinocyte Growth Factor Supplement+60 mM $CaCl_2$, supplied by Cascade Biologics, Inc.) for two days. Test compositions in a suitable solvent, such as 95% ethanol or DMSO, are added to selected wells in a range of concentrations and incubated for 16-24 hours. For the data reported herein, the solvent used was DMSO.

Cell lysing solution is prepared by addition of 3.0 mL Nonidet® P40, 1.0 mL CHAPS lysis buffer (see below), and 1.0 mL 10× TRAP buffer (see below) to 5.0 mL DNase-, RNase-free H2O. (DNase-, RNase-free water may be generated by DEPC (diethylpyrocarbonate) treatment or purchased from vendors such as Sigma.).

The morphology of treated cells is first observed under a microscope, to verify that there are no visual signs of irregular growth. Media is removed from the wells, and the cells are rinsed twice in PBS (Ca and Mg free). The dishes are chilled, preferably on ice, and cell lysis buffer (see below) is added (approx. 100 μl per well) and triturated by pipetting up and down several times. The cells are the incubated on ice for 1 hour.

| CHAPS Lysis Buffer | | |
| --- | --- | --- |
| Stock | For 1 mL | Final concn. |
| 1 M Tris-HCl pH 7.5 | 10 μl | 10 mM |
| 1 M $MgCl_2$ | 1 μl | 1 mM |
| 0.5 M EGTA | 2 μl | 1 mM |
| 100 mM AEBSF | 1 μl | 0.1 mM |
| 10% CHAPS[a] | 50 μl | 0.5% |
| BSA | 1 mg | 1 mg/ml |
| 100% Glycerol | 100 μl | 10% |
| DNase-, RNase-free $H_2O$ | 936 μl (to 1 mL) | |

[a]The CHAPS detergent is added just before use of the lysis buffer. In addition, AEBSF (4-(2-aminoethyl)-benzenesulfonyl fluoride HCl) is added to the lysis buffer just prior to the extraction step.

| 10X TRAP Buffer | | |
| --- | --- | --- |
| Stock | For 5 ml | Final concn. |
| 1M Tris-HCl, pH 8.3 | 1 ml | 200 mM |
| 1M $MgCl_2$ | 75 μl | 15 mM |
| 1M KCl | 3.15 ml | 630 mM |
| Tween 20 (Boehringer Mannheim) | 25 μl | 0.5% |
| 0.1M EGTA | 500 μl | 10 mM |
| 20 mg/ml BSA | 250 μl | 1 mg/ml |

The following materials are combined to generate a master PCR Mix.

| Stock | Per Reaction (40 μl) | Final concn.[a] |
| --- | --- | --- |
| 10X TRAP Buffer | 5.0 μl | 1X |
| 2.5 mM dNTPs | 1.0 μl | 50 μM |
| Cy5-TS Primer (0.1 mg/ml) | 0.2 μl | 0.4 ng/ml |
| ACX Primer (0.1 mg/ml) | 1.0 μl | 2 ng/ml |
| TSU2 Int. Std. (1 pg/ml) | 1.0 μl | 20 fg/ml |
| U2 Primer (0.1 mg/ml) | 1.0 μl | 2 ng/ml |
| Taq Polymerase (5 U/μl) | 0.4 μl | 2 units |
| DNase-, RNase-free $H_2O$ | 30.4 μl (to 40 μl total) | |

[a]Based on final volume of 4O μl PCR mix plus 10 μl cell lysate = 50 μl.

The PCR mix includes the following components: Cy5-TS primer, a 5'-Cy5 labeled oligonucleotide having the sequence 5'-AAT CCG TCG AGC AGA GTT-3' (SEQ ID NO:1), is a telomerase substrate. Depending on the telomerase activity of the medium, telomer repeats (having the sequence . . . AGGGTT . . . ) will be added to the substrate, to form telomerase extended products, also referred to as telomerase products or TRAP products. The ACX primer, having the sequence 5'-GCG CGG CTT ACC CTT ACC CTT ACC CTA ACC-3' (SEQ ID NO: 2), is an anchored return primer that hybridizes to the telomerase extended products.

The TSU2 internal standard, an oligonucleotide having the sequence 5'-AAT CCG TCG AGC AGA GTT AAA AGG CCG AGA AGC GAT-3'; SEQ ID NO:3), an extension of the TS primer sequence, is added in a small controlled quantity for quantitation purposes. The U2 primer, having the sequence 5'-ATC GCT TCT CGG CCT TTT (SEQ ID NO:4), is a return primer designed to hybridize to the 3' region of the internal standard.

A sample of cell lysate (10 μL) is added to 40 μL of this PCR mix in a reaction tube, and the mixture is incubated at room temperature (30° C.) for 30 minutes. PCR is carried out by incubating the mixture at the following temperatures for the times indicated: 94° C./30 sec, 60° C./30 sec, and 72° C./30 sec; repeating this three-step cycle to conduct 20-30, preferably 31 cycles.

Loading dye containing e.g. bromophenol blue and xylene cyanol is added, and the samples are subjected to 10-15% non-denaturing PAGE in 0.6×TBE, until the bromophenol blue runs off the gel. Product formation is observed, e.g. by using a fluoroimager for detection of CY5-labeled telomerase products (maximal excitation at 650 nm; maximal emission at 670 nm).

The final amount of TSU2 internal standard after amplification is generally 5-10 amol per 50 μl reaction mixture. This internal control gives a specific 36-mer PCR amplification product that appears as a distinct band on the gel below the first telomer addition product (that is, the product of one telomer addition to the TS oligonucleotide, followed by amplification with the ACX return primer). This internal control band can be used to normalize the PCR amplifications from different samples.

The relative number of telomerase product molecules (TM) generated in the assay is determined according to the formula below:

$$TM = (T_{TRAP\ Products} - T_{BKD1})/(T_{int\ Std} - T_{BKD2})$$

where: $T_{TRAP\ Products}$ is the total intensity measured on the gel for all telomerase products, $T_{BKD1}$ is the background intensity measured in a blank lane for an area equivalent in size to that encompassed by the telornierase products, $T_{int\ Std}$ is the intensity for the internal standard band, and $T_{BKD2}$ is the background intensity measured in a blank lane for ane area equivalent in size to that encompassed by the internal standard band. The resulting number is the number of molecules of telomerase products generated for a given incubation time, which, for the purposes of determining TM, is designated herein as 30 minutes.

Preferred compounds of formulas I, II or III as described above are able to produce, at a concentration of 1 μg/ml or less, a level of telomerase activity in fibroblasts or keratinocytes at least 25% greater than the level of such activity seen in a solvent control. More preferably, the compound is able to produce, at a concentration of 1 μg/ml or less, a telomerase activity at least 50% greater than seen in a solvent control. Even more potent activities may be appropriate for some applications, such as compounds that produce telomerase activities at least about 75%, 100% or 500% greater than the level of such activity seen in a solvent control, as measured in the described TRAP assay, at a concentration of 1 μg/ml or less.

B. Exemplar TRAP Assay Results

Effectiveness in increasing telomerase activity was evaluated for compounds of formula I above in various concentrations. Assays were carried out in HEKneoP cells (neonatal keratinocytes), according to the protocol described above. Concentrations ranged from approx. 0.03 μM to 10 μM in DMSO.

Figure 2:
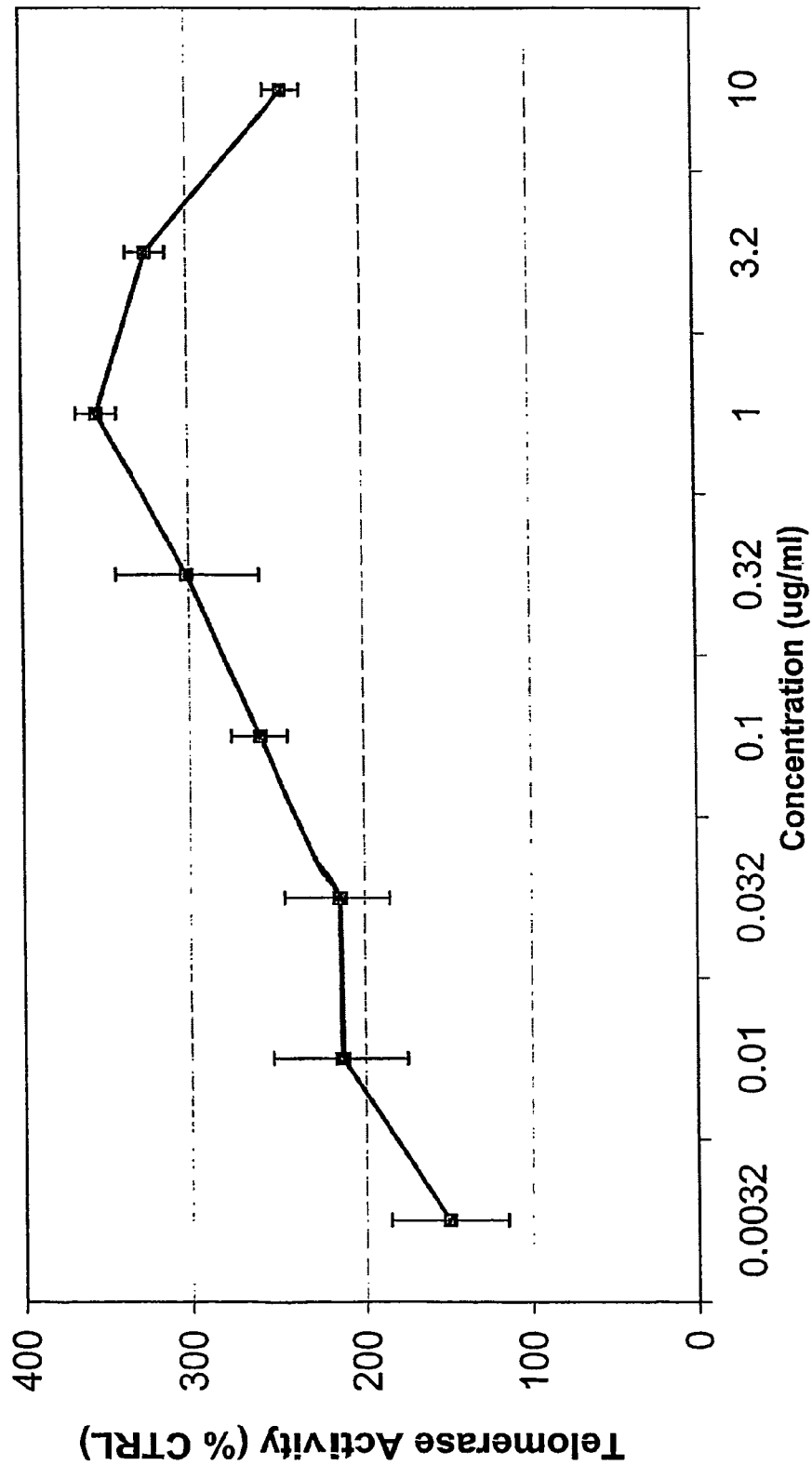
FIG. 2 shows an increase of telomerase activity in neonatal keratinocytes treated with 2 (cycloastragenol), as measured in a TRAP assay.
Figure 3:
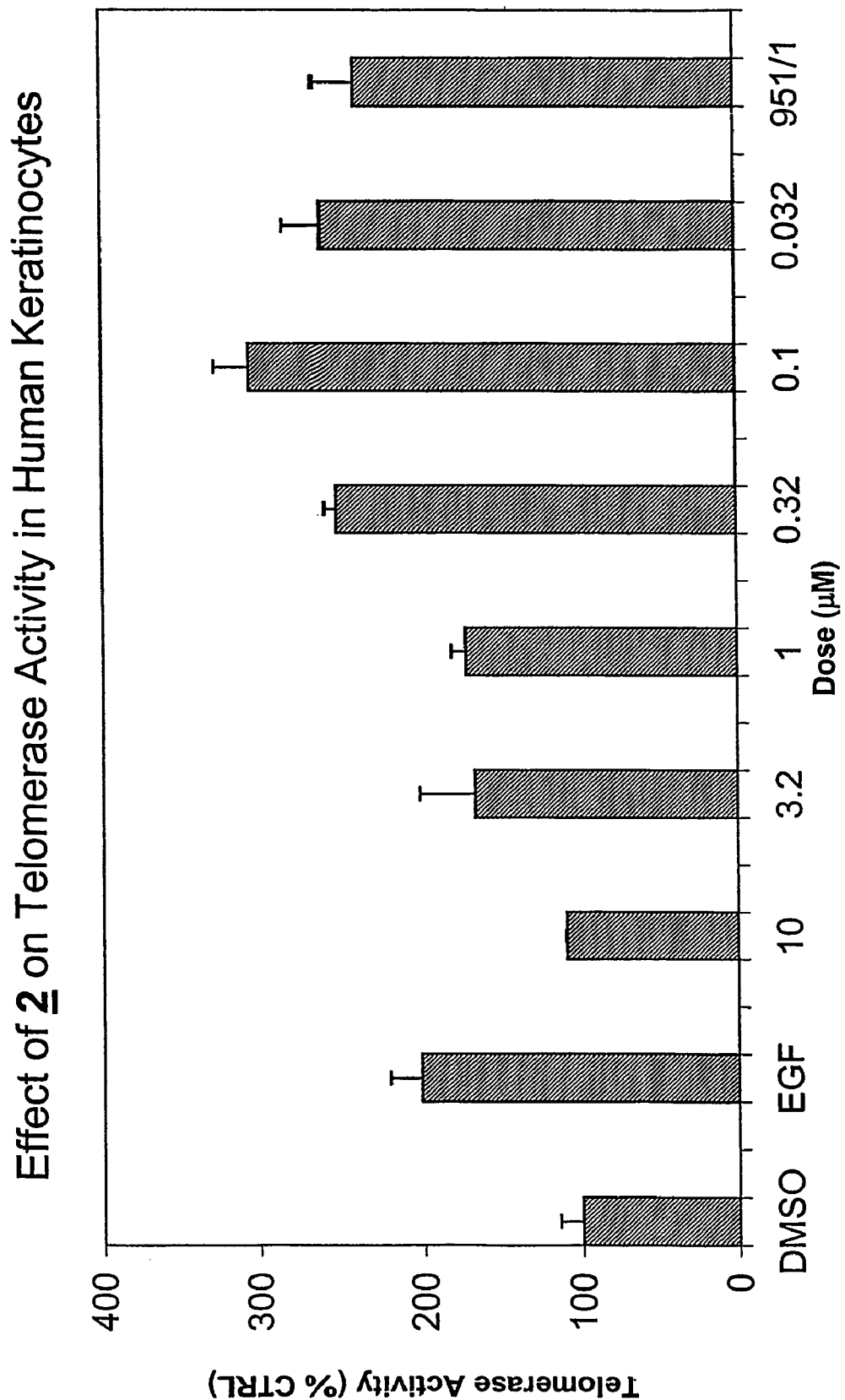
FIG. 3 shows an increase in telomerase activity in neonatal keratinocytes by 1 (astragaloside IV), in comparison with EGF (10 nM) and a solvent control, as measured in a TRAP assay.

As shown in FIG. 2, for compositions containing compound 1 (astragaloside IV), telomerase activity increased with increasing concentration, up to about 360% of control at 1.0 μM, then decreased as the concentration was increased further to 10 μM. As shown in FIG. 2, for compositions containing 2 (cycloastragenol), telomerase activity increased to about 300% of control at 0.1 μM (compared to about 200% in cells treated with 10 nM EGF (epidermal growth factor)), then decreased with further increases in concentration.

Table 1 gives, for compositions containing each of the compounds shown in FIGS. 1A-G, the minimum effective concentration (MEC) of the compound that produced a level of telomerase activity twice that seen in a DMSO control (i.e. 100% greater).

TABLE 1

| Designation | Name | MEC, μM |
|---|---|---|
| 1 | astragaloside IV | 0.01 |
| 2 | cycloastragenol | 0.01 |
| 3 | astragenol | 0.03 |
| 4 | astragaloside IV 16-one | 0.03 |
| 5 | 2OR,24S-epoxy-3β,16β,25-trihydroxy-9β-methyl-19-norlanost-1,5-diene | 0.10 |
| 6 | cycloastragenol 6-β-D-glucopyranoside | 3.2 |
| 7 | cycloastragenol 3-β-D-xylopyranoside | 3.2 |
| 8 | ginsenoside RH1 | 10 |

C. Wound Healing Assay Protocol

The compounds of formula I-III can be used to promote healing of wounds, burns, abrasions or other acute or chronic conditions of the epidermis, as discussed further below. As used herein, "wound healing activity as measured in a scratch assay" refers to the activity as measured in keratinocytes or fibroblasts according to the following protocol, and expressed as the value of WH shown in the formula below.

Cells are plated in flasks ($5 \times 10^5$ cells per flask) and cultured for two days in a humidified chamber at 5% $CO_2$, 37° C. To create the "wound", a 2 ml plastic pipette is gently dragged to "scratch" the cell surface. The ideal wound is approximately 2-3 mm wide and 50 mm long (along the long axis of the tissue culture flask). The cells are retreated with medium containing either vehicle (DMSO; control sample) or test compositions at multiple concentrations. A wound area is identified, the flask marked, and the appearance of the cells documented photographically over 3-4 days continued culturing of the cells.

Amount of wound closure is determined by measuring the width of the wound over time for compound-treated samples relative to vehicle-treated or other control cells. Measurements are made from the photographs taken for each of the samples on days 1 (immediately after scratching), 2, 3, and 4. Percentage of wound healing (also expressed as "wound healing activity") is calculated by the following formula:

$$WH = 100 - [100 \times W_n/W_0],$$

where $W_n$ is the width of the wound on day n and $W_0$ is the width of the wound on day one (i.e. immediately after scratching).

Preferred compounds of formula I-III as described above are able to produce, at a concentration of 1 μg/ml or less, an amount of wound closure (wound healing activity) in a scratch assay of keratinocytes or fibroblasts, as described above, which is at least 25% greater than that seen in untreated or control cells. Even more potent activities may be appropriate for some applications, such as compounds that produce, at a concentration of 1 μg/ml or less, an amount of wound closure in a scratch assay of keratinocytes or fibroblasts which is at least about 50% or 100% greater than that seen in untreated or control cells.

D. Exemplary Scratch Assay Results

Figure 4:
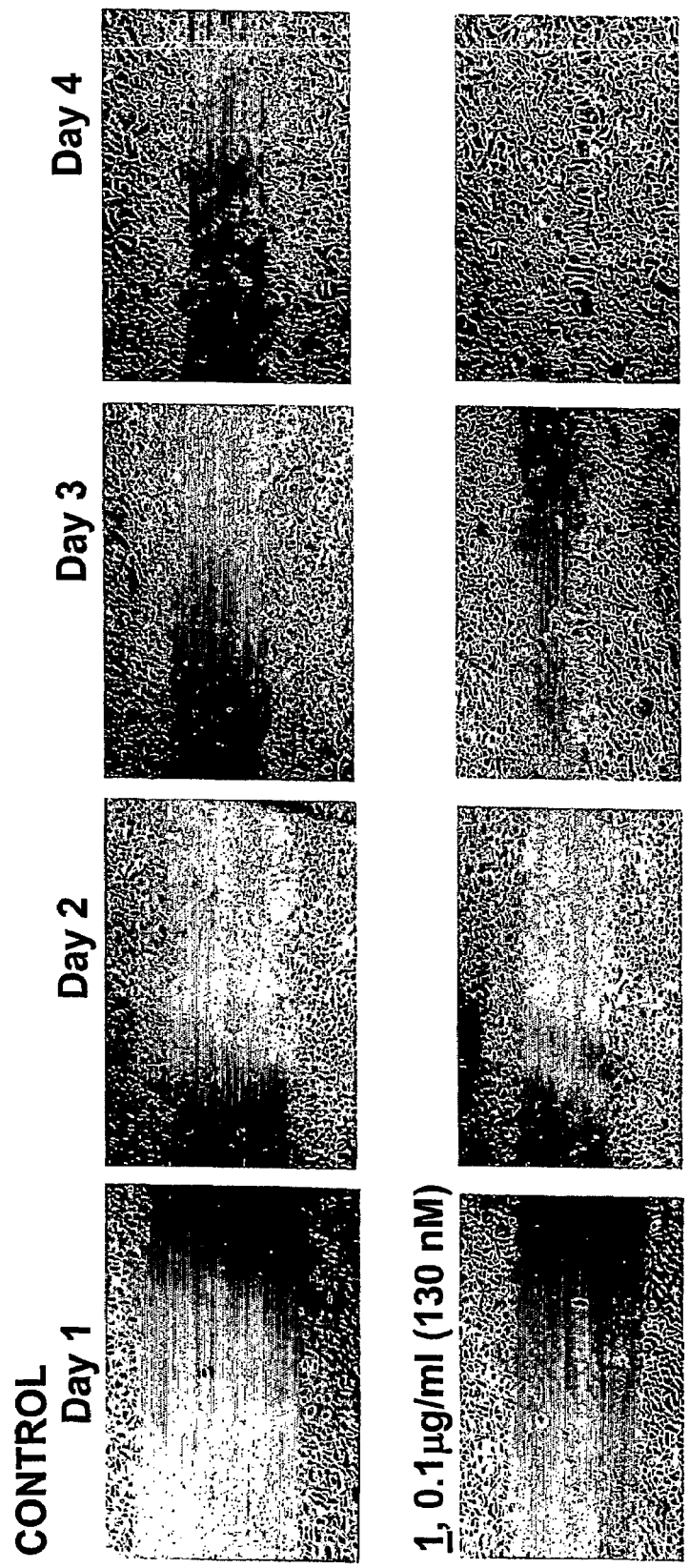
FIG. 4 is a series of computer-generated images showing wound healing activity of 1 (astragaloside IV) in aging adult keratinocytes, as measured in a "scratch assay".
Figure 5:
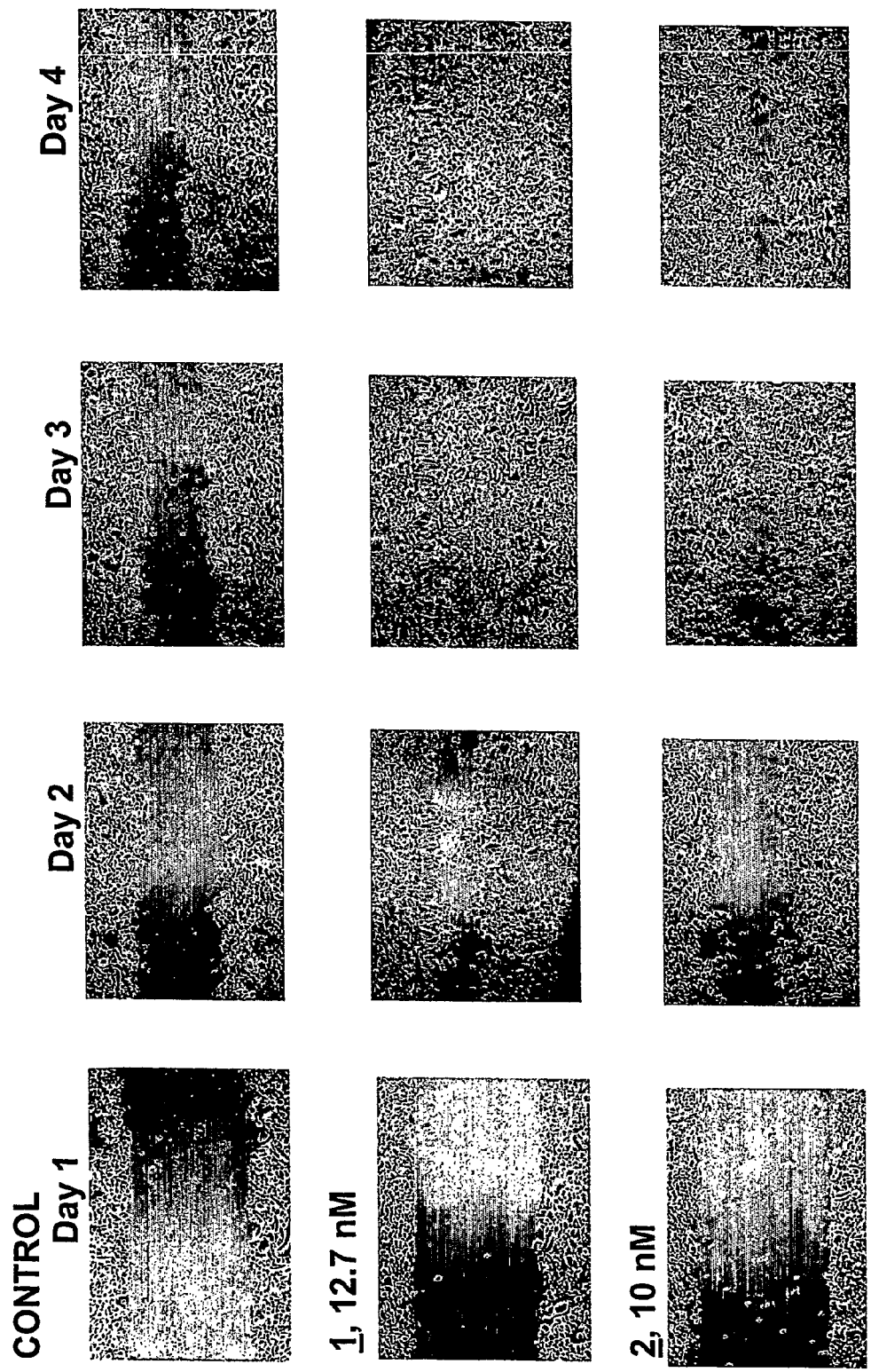
FIG. 5 is a series of computer-generated images showing wound healing activity of 1 (astragaloside IV) and 2 (cycloastragenol) in young neonatal keratinocytes.

Wound healing activity of invention compounds 1 (astragaloside IV) and 2 (cycloastragenol) was evaluated in aging keratinocytes, via a scratch assay as described above. Results of a typical assay are shown in FIG. 4, where the top row of images shows control cells (treated with solvent, DMSO), and the bottom row shows cells treated with 0.1 μg/ml (about 0.13 μM) 1 in the same solvent. The treated cells were confluent at day 4, in contrast to the control cells, in which a sizable "wound" remained at day 4. Similar results were seen with this composition and with 0.01 μM 2 (cycloastragenol) in young keratinocytes, as shown in FIG. 5.

Figure 6:
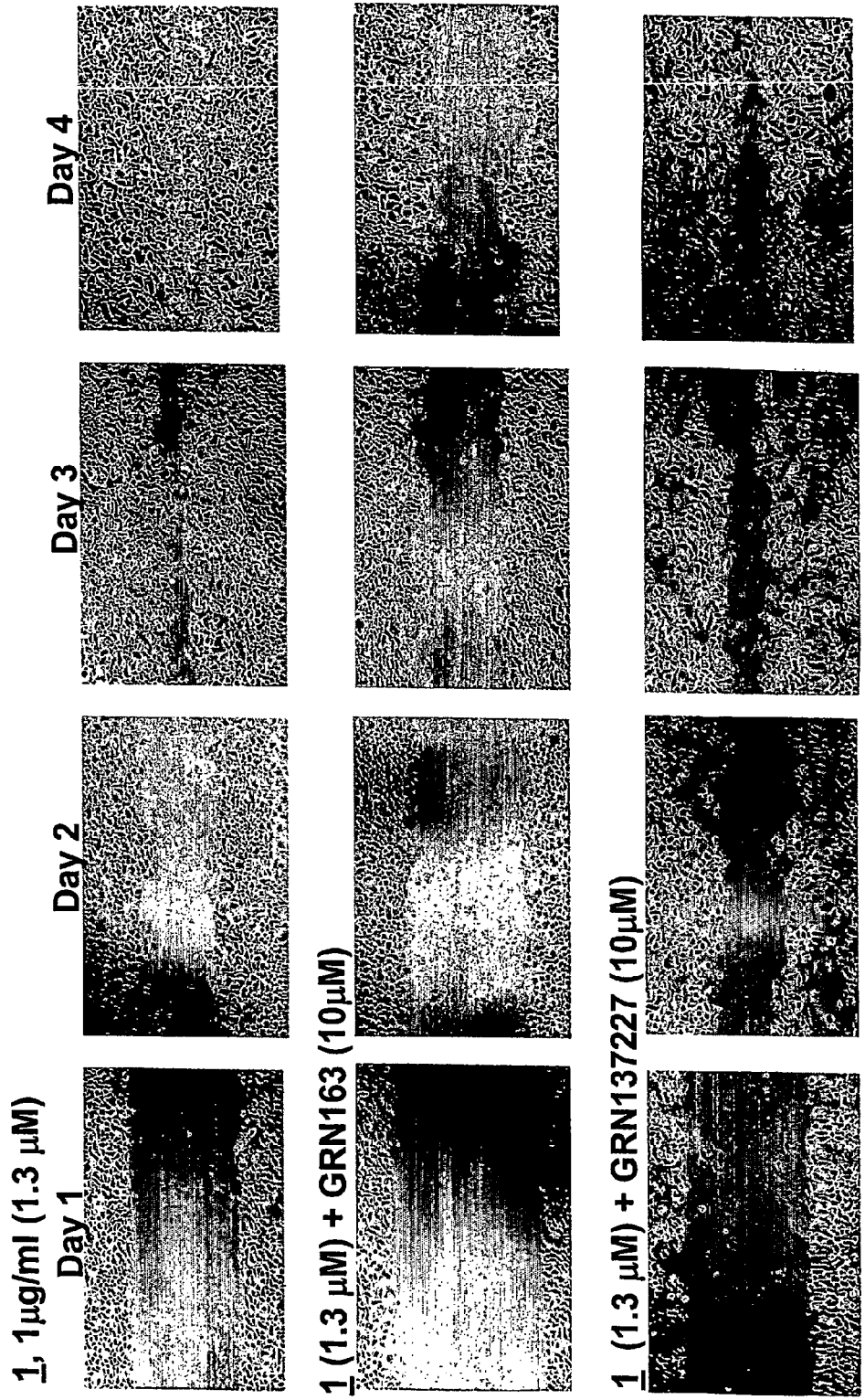
FIG. 6 is a series of computer-generated images showing wound healing activity of 1 (astragaloside IV) in aging keratinocytes, alone and in the presence of a telomerase inhibiting oligonucleotide (GRN163) or a control oligonucleotide (GRN137227).

FIG. 6 shows the wound healing activity of a composition containing 1 (astragaloside IV) in aging adult keratinocytes, as measured in a similar assay, in the presence and absence of a telomerase inhibiting oligonucleotide (GRN163) and a control oligonucleotide (GRN137227). As shown, telomerase inhibiting oligo GRN163 blocks the wound healing effects of the 1 composition; the effect of control oligo GRN137226 is minimal. (GRN163 is a telomerase inhibitor oligonucleotide that targets the template region of the telomerase RNA component. Specifically, GRN163 is a 13-mer N3'→P5' thiophosphoramidate oligonucleotide, described in detail in PCT Pubn. No, WO 01/18015. GRN137227 is a 13-mer N3'→P5' thiophosphoramidate control oligonucleotide having a mismatched sequence.)

Table 2 below shows WH values (wound healing activity) for compounds 1 and 2 employed in the scratch assays shown in FIGS. 5 and 6, based on the results of those assays, using the formula shown above.

TABLE 2

| | Approx. wound width (arbitrary units) | | | | | |
|---|---|---|---|---|---|---|
| | Day 1 cntl | Day 4 cntl | Day 1 test | Day 1 test | $WH_{cntrl}$ | $WH_{test}$ |
| FIG. 4 (1) | 22 | 10 | 17 | 0 | 54.5 | 100 |
| FIG. 5 (1) | 19 | 9 | 18 | 0 | 52.6 | 100 |
| FIG. 5 (2) | 19 | 9 | 21 | 2 | 52.6 | 90.5 |

FIG. 7 graphically illustrates wound closure as percent of control for invention compound 1 (astragaloside IV) in aging neonatal keratinocytes, in the presence and absence of a telomerase inhibitor (GRN163), and in comparison with 50 ng/mL (approx. 2 mL) PDGF (platelet derived growth factor). As shown, the effectiveness of 1 was comparable to that of PDGF, and was again blocked by the addition of GRN163.

V. Selection of Additional Compounds

The invention also provides methods of selecting additional compounds effective to increase telomerase activity, by screening derivatives of compounds of formula I, II, or III in a TRAP assay as described herein. In this aspect, a "derivative" includes a compound produced by modification of a compound of formula I, II, or III in one or more of the following ways: conversion of a hydroxyl group to a lower alkyl carbamate, halogen, thiol, lower alkyl thioether, amino, lower alkylamino, lower alkyl amide, aldehyde, or keto group; addition of a lower alkyl group to such an aldehyde or keto group, or to an existing keto group (e.g. alkylation, with formation of a further hydroxyl group); addition of halogen, hydroxyl, and/or hydrogen to a carbon-carbon double bond; removal of a hydroxyl group (i.e., conversion to hydrogen); and inversion of stereochemistry at one or more chiral centers, preferably an oxygen-bearing chiral center. As used herein, a "derivative" produced by such modification(s) excludes the compounds of formulas I, II and III themselves as defined above.

All of these modifications can be accomplished using standard synthetic methods, employing well known synthetic reactions such as nucleorphilic substitution, which may include conversion of a hydroxyl group to a better leaving group, such as a tosylate; esterification; alkylation; oxidation; reduction; halogenation; hydration; hydrogenation; etc.

A derivative of a compound of formula I, II, or III, formulated in a suitable solvent medium at one more concentrations, is screened in a TRAP assay of keratinocytes or fibroblasts as described above. Preferred derivatives for selection include those that are effective, when formulated in a solvent at a concentration of 1 μg/ml or less, to produce a level of telomerase activity in keratinocytes or fibroblasts, as measured in a TRAP assay, at least 50% greater than that measured in said cells treated with said solvent.

Alternatively, or in addition, a derivative of formula I, II, or III, formulated in a suitable solvent medium at one more concentrations, is assayed for wound healing activity in a scratch assay as described above. Preferred derivatives for selection include those having wound healing activity, at a concentration of 1 μg/ml or less, at least 25% greater, and more preferably at least 50% greater, than that of a solvent control.

VI. Therapeutic Indications and Treatment Methods

The present invention provides methods for increasing telomerase activity in a cell, by contacting a cell or tissue with a formulation of an isolated compound of formula I, II or III as disclosed in Section III above, in an amount effective to increase telomerase activity in the cell. The method may include the preliminary step of identifying a cell or tissue in which an increase telomerase activity is desired. The cell may be in culture, i.e. in vitro or ex vivo, or within a subject or patient in vivo.

Benefits to be realized from an increase in telomerase activity in a cell or tissue include, for example, enhancement of the replicative capacity and/or life span of the contacted cells. The method may further comprise diagnosing a condition in a subject or patient wherein an increase in telomerase activity in cells or tissue of the patient is desired; e.g., diagnosing a disease subject to treatment by an increase in telomerase activity in cells or tissue. Accordingly, the invention provides methods of treating a condition in a patient, by increasing telomerase activity in cells or tissue of said patient, the method comprising administering to a subject in need of such treatment an effective amount of a compound of formula I, II or III as disclosed in Section II above. An "effective amount" refers to an amount effective to increase telomerase activity in the cells or tissue of the patient, such that a therapeutic result is achieved.

Such conditions may include, for example, conditions associated with cellular senescence or with an increased rate of proliferation of a cell in the absence of telomerase, which leads to accelerated telomere repeat loss. By "increased rate of proliferation" is meant a higher rate of cell division compared to normal cells of that cell type, or compared to normal cells within other individuals of that cell type. The senescence of those groups of cells at an abnormally early age can eventually lead to disease (see West et al., U.S. Pat. No. 6,007, 989).

Various disease states exist in which an increase in telomerase activity in certain cell types can be beneficial. Accordingly, the invention provides methods of treating in a patient a condition selected from the following, by increasing telomerase activity in the cells of the patient, comprising administering to a subject in need of such treatment, an effective amount of a compound of formula I, II, or III as described above. In some cases, the condition may also be subject to treatment by ex vivo cell therapy, as described further below, employing the associated cell types (indicated in parenthesis).

(a) Alzheimer's disease, Parkinson's disease, Huntington's disease, and stroke (cells of the central nervous system, including neurons, glial cells, e.g. astrocytes, endothelial cells, fibroblasts), (b) age-related diseases of the skin, such as dermal atrophy and thinning, elastolysis and skin wrinkling, sebaceous gland hyperplasia or hypoplasia, senile lentigo and other pigmentation abnormalities, graying of hair and hair loss or thinning, or chronic skin ulcers (fibroblasts, sebaceous gland cells, melanocytes, keratinocytes, Langerhan's cells, microvascular endothelial cells, hair follicle cells), (c) degenerative joint disease (cells of the articular cartilage, such as chondrocytes and lacunal and synovial fibroblasts), (d) osteoporosis and other degenerative conditions of the skeletal system (cells of the skeletal system, such as osteoblasts, bone marrow stromal or mesenchymal cells, osteoprogenitor cells), (e) age- and stress-related diseases of the vascular system including atherosclerosis, calcification, thrombosis, and aneurysms (cells of the heart and vascular system, including endothelial cells, smooth muscle cells, and adventitial fibroblasts), (f) age-related macular degeneration (cells of the eye, such as pigmented epithelium and vascular endothelial cells), (g) AIDS (HIV-restricted $CD8^+$ cells); and (h) age- and stress-related immune system impairment, including impairment of tissue turnover, which occurs with natural aging, cancer, cancer therapy, acute or chronic infections, or with genetic disorders causing accelerated cell turnover, and related anemias and other degenerative conditions (other cells of the immune system, including cells in the lymphoid, myeloid, and erythroid lineages, such as B and T lymphocytes, monocytes, circulating and specialized tissue macrophages, neutrophils, eosinophils, basophils, NK cells, and their respective progenitors).

In addition to the cell types noted above, further cell types in which an increase in telomerase activity can be therapeutically beneficial include, but are not limited to, cells of the liver, endocrine and exocrine glands, smooth musculature, or skeletal musculature.

As an example, in the case of HIV-infected individuals, $CD8^+$ cell turnover is increased as these cells attempt to control the level of HIV-infected $CD4^+$ cells. In AIDS (item (g) above), disease is believed to be caused by the early senescence of HIV-restricted $CD8^+$ cells. The aging of such cells is attributed not simply to abnormal amount of loss of telomere sequences per cell doubling, but, in addition, to the increased replicative rate of the cells, such that telomere attrition is greater than normal for that group of cells. The invention thus provides methods of treating an HIV infected subject, and more particularly of reducing early senescence of HIV-restricted $CD8^+$ cells in an HIV infected subject, by administering to a subject in need of such treatment an effective amount of a compound of formula I, II or III as disclosed in Section II above.

An increase in telomerase activity can benefit non-dividing cells as well as proliferating cells, e.g. in conditions associated with increased susceptibility to cell death due to stress, such as ischemia in heart failure or in stroke (see e.g. Oh and Schneider, *J Mol Cell Cardiol* 34(7):717-24; Mattson, *Exp Gerontol.* 35(4):489-502). The invention thus provides methods of reducing stress- or DNA-damage-induced cell death in a subject, such as a subject experiencing ischemic conditions in tissue due to heart failure or stroke, by increasing telomerase activity in cells of the subject, comprising administering to a subject in need of such treatment an effective amount of a compound of formula I, II or III as disclosed in Section II above. As noted above, the method may include the preliminary step of diagnosing in the subject the indicated condition.

In another aspect, the compositions may be used for the treatment of individuals in which one or more cell types are limiting in that patient, and whose life can be extended by extending the ability of those cells to continue replication or resist stress-induced cell death. One example of such a group of cells is lymphocytes present in Down's Syndrome patients. The invention thus provides a method of enhancing replicative capacity and/or life span of lymphocytes present in a Down's Syndrome patient, by increasing telomerase activity in said cells of the patient, comprising administering to such a patient an effective amount of a compound of formula I, II or III as disclosed in Section II above. The compositions may also be used to improve resistance to stress-induced cell death occurring during normal aging.

In a further aspect of the invention, increasing telomerase activity is effective to promote healing of wounds, burns, abrasions or other acute or chronic conditions of the epidermis. The invention thus provides a method of treating an acute or chronic condition of the epidermis, by administering to a patient in need of such treatment, preferably topically to the affected area, an effective amount of a formulation of an isolated compound of formula I, II or III as disclosed in Section II above.

As used herein, an "acute or chronic condition of the epidermis" includes acute conditions such as lesions suffered in trauma, burns, abrasions, surgical incisions, donor graft sites, and lesions caused by infectious agents, and chronic conditions such as chronic venous ulcer, diabetic ulcer, compression ulcer, pressure sores, and ulcers or sores of the mucosal surface. Also included are skin or epithelial surface lesions caused by a persistent inflammatory condition or infection, or by a genetic defect (such as keloid formation and coagulation abnormalities). See, for example, PCT Pubn. No. WO 02/91999.

Desirable effects of an increase in telomerase activity in such treatment include cell proliferation or migration at the treatment site, epithelialization of the surface, closure of a wound if present, or restoration of normal physiological function. By "epithelialization" or "reepithelialization" of a treatment site is meant an increase in density of epithelial cells at the site as a result of the applied therapy.

The method may also be used to enhance growth of engrafted cells. Desirable effects of an increase in telomerase activity in such treatment include coverage of the treatment site, survival of engrafted cells, lack of immune rejection, closure of a wound if present, or restoration of normal physiological function. Engrafted cells may participate in wound closure either by participating directly in the healing process (for example, becoming part of the healed tissue), or by covering the wound and thereby providing an environment that promotes healing by host cells.

The invention also contemplates manipulation of the skin and repair of any perceived defects in the skin surface for other purposes, such as cosmetic enhancement.

In a further aspect, the methods and compositions of the invention can be used to enhance replicative capacity and/or extend life span of cells in culture, e.g. in ex vivo cell therapy or in monoclonal antibody production, by increasing telomerase activity in the cells. Increasing telomerase activity increases the replicative capacity of such cells by slowing telomere repeat loss and/or improving resistance to stress-induced cell death during cell proliferation.

In the case of ex vivo applications, an effective amount of a compound of formula I, II or III as described above is added to explant cells obtained from a subject. An "effective amount" refers to an amount effective to increase telomerase activity in the cells, thereby increasing the replicative capacity and/or life span of the cells.

The explant cells may include, for example, stem cells, such as bone marrow stem cells (U.S. Pat. No. 6,007,989), bone marrow stromal cells (Simonsen et al., *Nat Biotechnol* 20(6):592-6, 2002), or adrenocortical cells (Thomas et al, *Nat Biotechnol* 18(1):39-42, 2000). Disease conditions such as those noted in items (a)-(g) above may also be subject to ex vivo cell-based therapy. Examples include the use of muscle satellite cells for treatment of muscular dystrophy, osteoblasts to treat osteoporosis, retinal pigmented epithelial cells for age-related macular-degeneration, chondrocytes for osteoarthritis, and so on.

For example, the recognition that functional $CD8^+$ cells are limiting in AIDS patients to control the expansion of infected $CD4^+$ cells allows a therapeutic protocol to be devised in which 1-HIV-restricted $CD8^+$ cells are removed from an HIV-infected individual at an early stage, when AIDS is first detected, stored in a bank, and then reintroduced into the individual at a later stage, when that individual no longer has the required $CD8^+$ cells available. Thus, an individual's life can be extended by a protocol involving continued administration of that individual's limiting cells at appropriate time points. These appropriate points can be determined by following $CD8^+$ cell senescence, or by determining the length of telomeres within such $CD8^+$ cells, as an indication of when those cells will become senescent. In accordance with the invention, the stored cells can be expanded in number in the presence of an agent which slows telomere repeat loss, i.e. compound of formula I, II or III as disclosed in Section II above.

Accordingly, the invention provides methods of ex vivo cell based therapy, which include obtaining a cell population from a subject, and expanding the cell population ex vivo, wherein the cell population is treated with a compound of formula I, II or III as disclosed in Section II above, in an amount effective to increase telomerase activity and thereby enhance the replicative capacity and/or life span of the cell population. The method generally includes diagnosing in a subject a condition subject to treatment by ex vivo cell based therapy, such as those noted above.

In a further embodiment, the invention provides a method of stem cell proliferation, wherein a stem cell population is treated with a compound of formula I, II or III as disclosed in Section II above, in an amount effective to increase telomerase activity and thereby enhance the replicative capacity and/or life span of the cell population.

VII. Formulations and Methods of Administration

The invention encompasses methods of preparing pharmaceutical compositions useful for increasing telomerase activity in a cell and/or promoting wound healing. Accordingly, an isolated compound of formula I, II or III as described in Section II is combined with a pharmaceutical excipient, and optionally with other medicinal agents, adjuvants, and the like, which may include active and inactive ingredients. The compositions may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, or the like. The formulations may be provided in unit dosage forms suitable for simple administration of precise dosages.

An isolated compound of formula I, II or III may also be formulated as a dietary supplement or nutraceutical, for oral administration. For a nutraceutical formulation, or an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. An isolated compound of formula I, II or III may also be incorporated into existing nutraceutical formulations, such as are available conventionally, which may also include an herbal extract, such as an extract of *Astragalus membranaceus*.

For use in wound healing or treatment of other acute or chronic conditions of the epidermis, a compound of formula I, II or III is formulated for topical administration. The vehicle for topical application may be in one of various forms, e.g. a lotion, cream, gel, ointment, stick, spray, or paste. These product forms can be formulated according to well known methods. They may comprise various types of carriers, including, but not limited to, solutions, aerosols, emulsions, gels, and liposomes. The carrier may be formulated, for example, as an emulsion, having an oil-in-water or water-in-oil base. Suitable hydrophobic (oily) components employed in emulsions include, for example, vegetable oils, animal fats and oils, synthetic hydrocarbons, and esters and alcohols thereof, including polyesters, as well as organopolysiloxane oils. Such emulsions also include an emulsifier and/or surfactant, e.g. a nonionic surfactant, such as are well known in the art, to disperse and suspend the discontinuous phase within the continuous phase.

The topical formulation typically contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components as known in the art, e.g. astringents, fragrances, pigments, skin penetration enhancing agents, sunscreens, etc.

The pharmaceutical compositions may also be formulated for administration par-enterally, transdermally, or by inhalation. An injectable composition for parenteral administration typically contains the active compound in a suitable IV solution, such as sterile physiological saline. The composition may also formulated as a suspension in a lipid or phospholipid, in a liposomal suspension, or in an aqueous emulsion.

For administration by inhalation, the active compound is formulated as solid or liquid aerosol particles. The formulation may also include a propellant and/or a dispersant, such as lactose, to facilitate aerosol formation. For transdermal administration, the active compound is preferably included in a transdermal patch, which allows for slow delivery of compound to a selected skin region, and which may also include permeation enhancing substances, such as aliphatic alcohols or glycerol.

Methods for preparing such formulations are known or will be apparent to those skilled in the art; for example, see *Remington's Pharmaceutical Sciences* (19$^{th}$ Ed., Williams & Wilkins, 1995). The composition to be administered will contain a quantity of the selected compound in a pharmaceutically safe and effective amount for increasing telomerase activity in the target cells or tissue.

Preferably, the pharmaceutical or nutraceutical composition contains at least 0.1% (w/v) of a compound of formula I, II or III as described above, preferably greater than 0.1%, up to about 10%, preferably up to about 5%, and more preferably up to about 1% (w/v). Choice of a suitable concentration depends on factors such as the desired dose, frequency and method of delivery of the active agent.

For treatment of a subject or patient, such as a mammal or a human patient, dosages are determined based on factors such as the weight and overall health of the subject, the condition treated, severity of symptoms, etc. Dosages and concentrations are determined to produce the desired benefit while avoiding any undesirable side effects. Typical dosages of the subject compounds are in the range of about 0.5 to 500 mg/day for a human patient, preferably about 1-100 mg/day. For example, higher dose regimens include e.g. 50-100, 75-100, or 50-75 mg/day, and lower dose regimens include e.g. 1-50, 25-50, or 1-25 mg/day. In specific embodiments, for example, the compound designated herein as 2 (cycloastragenol) is administered at a level of at least 1 mg/day, preferably at least 5 mg/day; or the compound designated herein as 1 (astragaloside IV) is administered at a level of at least 50 mg/day, preferably at least 100 mg/day.

Studies in support of the invention indicate that the compounds of formula I-III have excellent bioavailability and low toxicity. For example, a representative compound, cycloastragenol (2), was negative for reverse bacterial mutation potential in the Ames test, employing *Salmoniella Typhimurium* tester strains TA98, TA100, TA1535, TA 1537 and *E. coli* tester strain WP2 uvrA, at levels up to 5000 μg/plate. It was well-tolerated systemically in Sprague-Dawley rats, after single intravenous injections up to 10 mg/kg. No significant dose-dependent changes were observed for males or females in behavior (eating, drinking), gross weight, organ weights (heart, lung, liver, kidneys, adrenals and spleen), hematology or clinical chemistry.

EXAMPLES

Example 1

Conversion of Astragaloside IV (1) to Cycloastragenol (2)

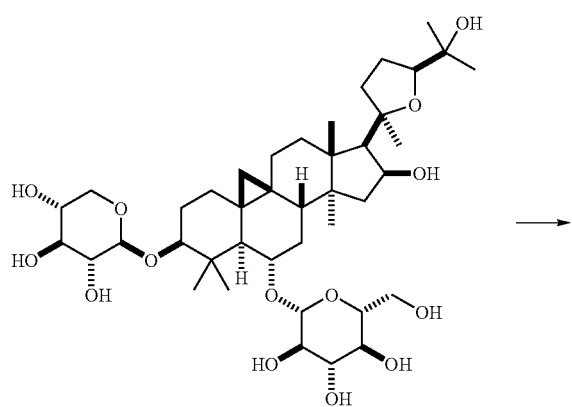

1

-continued

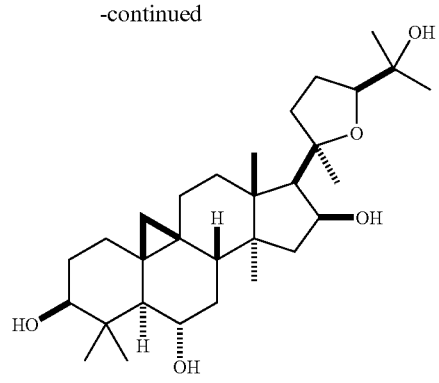

2

To astragaloside IV (1) (5.00 g, mmol) was added "HCl-MeOH 10" (TCI America) (500 mL) and the mixture was stirred at room temperature for 7 days. The reaction mixture was concentrated to about half volume under reduced pressure at 20° C. (do not heat). The mixture was partitioned into aqueous sodium bicarbonate and ethyl acetate. The aqueous layer was extracted with ethyl acetate again. The organic layers were combined, washed with saturated sodium chloride, dried on anhydrous sodium sulfate, and concentrated under reduced pressure. The residue was purified by column chromatography (20:1~14:1 chloroform/methanol). In order to replace the residual solvent with ethanol, the purified material was dissolved in ethanol and the solvent was removed under reduced pressure to afford 2 (2.1 g, 64%).

$^1$H NMR (CDCl$_3$) δ (ppm) 0.34 (d, J=4.7 Hz, 1H), 0.48 (d, J=4.3 Hz, 1H), 0.92 (s, 3H), 0.93 (s, 3H), 1.0-1.8 (m, 13H), 1.11 (s, 3H), 1.19 (s, 3H), 1.22 (s, 6H), 1.27 (s, 3H), 1.9-2.0 (m, 4H), 2.30 (d, J=7.8 Hz, 1H), 2.54 (q, J=11.8 Hz, 1H), 3.27 (m, 1H), 3.50 (m, 1H), 3.72 (t, J=7.4 Hz, 1H), 4.65 (q, J=7.4 Hz, 1H). ESI-MS m/z Positive 491 (M+H)$^+$, Negative 549 (M+AcO)$^-$. TLC (Merck, Kieselgel 60) Rf=0.33 (6:1 chloroform/methanol)

Example 2

Preparation of Compounds 5, 6 and 7 from Astragaloside IV (1): Removal of Glycosides from Astragaloside IV (1), with and without Concomitant Rearrangement

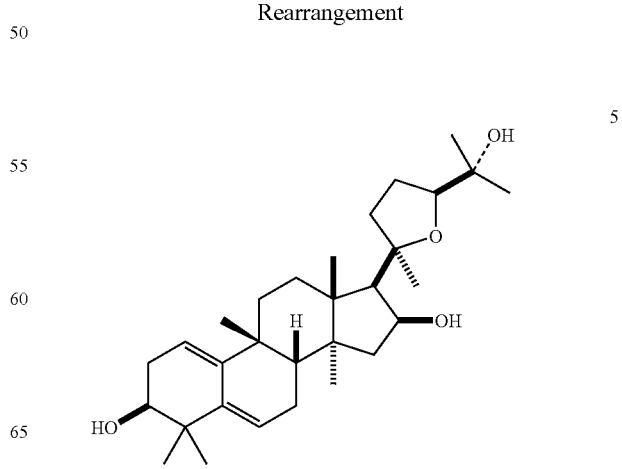

5

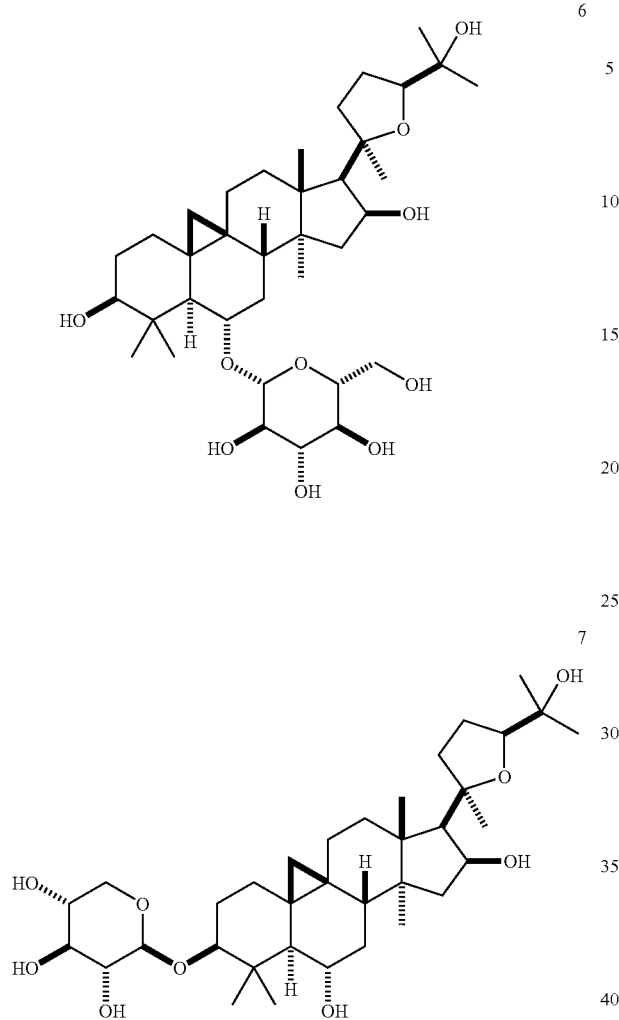

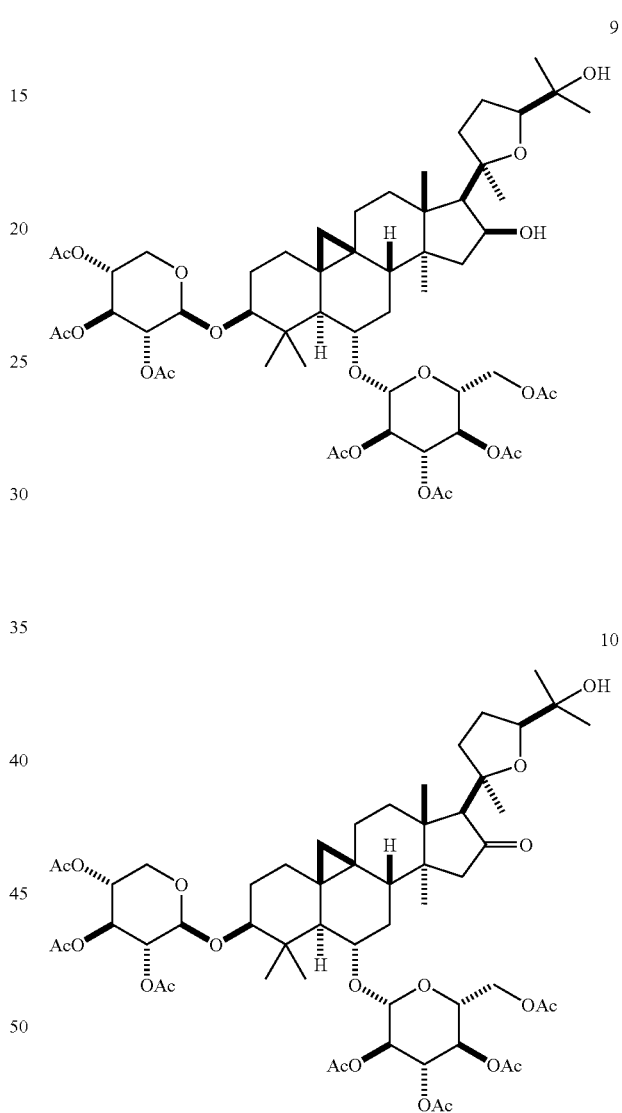

To a solution of astragaloside IV (1, 1.00 g, 1.28 mmol) in methanol (80 mL) was added sulfuric acid (0.4 mL), and the mixture was refluxed for 1.5 h. After cooling to room temperature, the mixture was poured into ethyl acetate and water. The organic layer was washed with brine and dried on anhydrous sodium sulfate. The solvent was removed under reduced pressure, and the residue was purified by silica gel column chromatography (20:1~10:1~7:1 chloroform/methanol) to afford the rearranged product 5 (24 mg, 4.0%), monoglycosides 6 (172 mg, 21%) and 7 (29 mg, 3.6%) and the aglycone, cycloastragenol (2) (326 mg, 52%).

GRN140724: ESI-MS m/z 623 M+H)$^+$ $C_{35}H_{58}O_9$=622

GRN140725: ESI-MS m/z 653 (M+H)$^+$ $C_{36}H_{60}O_{10}$=652

GRN140726: ESI-MS m/z 473 (M+H)$^+$ $C_{30}H_{48}O_4$=472. $^1$H NMR (400 MHz, CDCl$_3$) δ (ppm) 0.72, 0.85, 0.95, 1.05, 1.11, 1.17, 1.18, and 1.25 (s, 3H each), 0.9-2.1 (m, 13H), 2.20 (d, J=7.4 Hz, 1H), 2.4-2.6 (m, 2H), 3.42 (m, 1H), 3.70 (dd, J=7.8, 5.9 Hz, 1H), 4.63 (q, J=7.4 Hz, 1H), 5.45 (br s, 1H), 5.57 (br s, 1H).

Example 3

Acetylation of 1: Formation of 16-ketone 10

Compounds 9 and 10, below, were obtained according to the method of Kitagawa 1983b, cited above. Briefly, acetylation of astragaloside IV (1) provided 9, together with a smaller amount of the 16-acetate counterpart Pyridinium chlorochromate oxidation of 9 gave 10.

Example 4

Preparation of 4 (See FIG. 1) by Deacylation of 10

To a solution of 10, above (10 mg, 0.0093 mmol) in methanol was added sodium borohydride (10 mg, 0.26 mmol), and the mixture was stirred at room temperature overnight. The mixture was diluted with chloroform (3 mL) and directly subjected to silica gel column chromatography (3:1 chloroform/methanol) to afford 4 (8.0 mg, quant.). ESI-MS m/z 783 (M+H)$^+$ $C_{41}H_{66}O_{14}$=782.

Example 5

Formation of Trione 11 of Cycloastragenol 2

The 3,6,16-trione derivative 11 of cycloastragenol was obtained by $CrO_3$ oxidation of 2, according to the method of Kitagawa et al., *Chem. Pharm. Bull.* 31(2):689-697 (1983a).

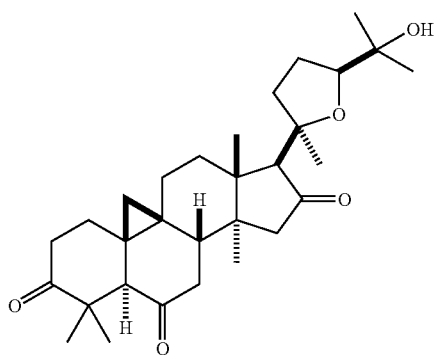

11

Example 6

Acylation of 3- or 6-hydroxyl Group of Cycloastragenol (2)

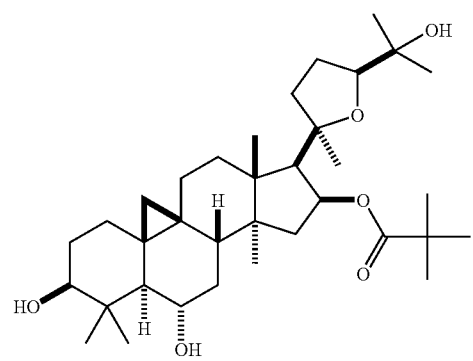

12

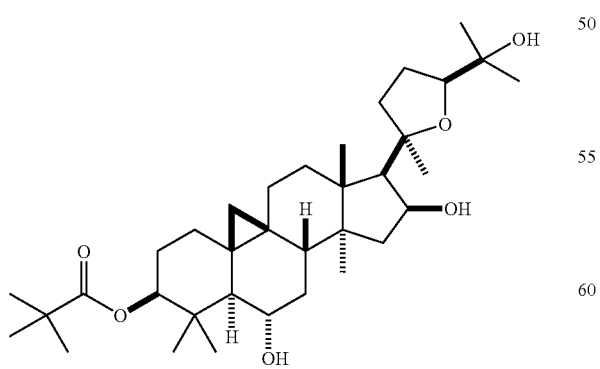

13

To a solution of cycloastragenol (2) (50 mg, 0.10 mmol) in dichloromethane (5 mL) were added triethylamine (0.030 mL, 0.22 mmol) and pivaloyl chloride (0.014 mL, 0.12 mmol), and the mixture was stirred at 0° C. overnight. The mixture was directly subjected to silica gel column chromatography (1:1~1:2 hexane/ethyl acetate) to give 12 (17 mg, 30%) and 13 (3.3 mg, 2.9%).

12: ESI-MS m/z 575 (M+H)$^+$ $C_{35}H_{58}O_6$=574. $^1$H NMR (400 MHz, CDCl$_3$) δ (ppm) 0.32 (d, J=4.7 Hz, 1H), 0.49 (d, J=4.7 Hz, 1H), 0.92 (s, 3H), 0.95 (s, 3H), 1.07 (s, 3H), 1.1-2.0 (m, 17H), 1.15 (s, 9H), 1.18 (s, 3H), 1.21 (s, 3H), 1.34 (s, 6H), 2.19 (dd, J=13.7, 9.8 Hz, 1H), 2.36 (d, J=7.8 Hz, 1H), 3.27 (m, 1H), 3.51 (td, J=9.4, 3.5 Hz, 1H), 3.71 (t, J=7.4 Hz, 1H), 5.32 (td, J=7.8, 4.7 Hz, 1H).

13: ESI-MS m/z 575 (M+H)$^+$ $C_{35}H_{58}O_6$=574. $^1$H NMR (400 MHz, CDCl$_3$) δ (ppm) 0.35 (d, J=4.3 Hz, 1H), 0.51 (d, J=4.3 Hz, 1H), 0.92 (s, 3H), 1.0-2.0 (m, 17H), 1.03 (s, 3H), 1.09 (s, 3H), 1.12 (s, 3H), 1.17 (s, 9H), 1.21 (s, 3H), 1.24 (s, 3H), 1.28 (s, 3H), 2.29 (d, J=7.8 Hz, 1H), 2.53 (m, 1H), 3.50 (m, 1H), 3.73 (t, J=7.2 Hz, 1H), 4.50 (dd, J=10.9, 4.3 Hz, 1H), 4.65 (m, 1H).

Example 7A

Acetylation of Secondary Hydroxyls of Cycloastragenol (2)

This reaction was carried out according to the method of Kitagawa 1983a, cited above. Briefly, acetylation with acetic anhydride/pyridine gave a mixture of 14 (major product) and 15 (minor product).

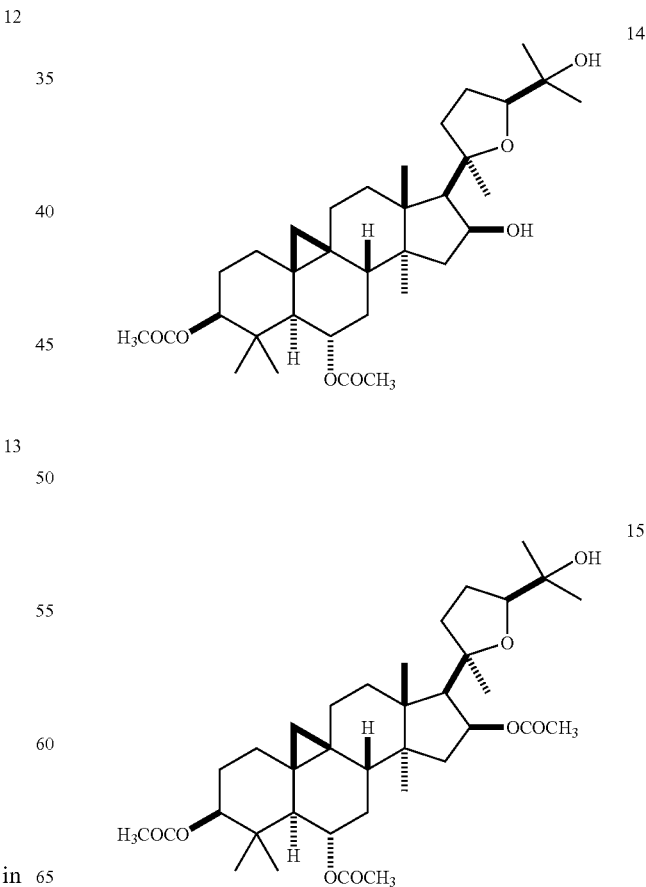

Example 7B

Methylation of 3,6-diacetyl Cycloastragenol (14), with Retention of Acetyl Groups

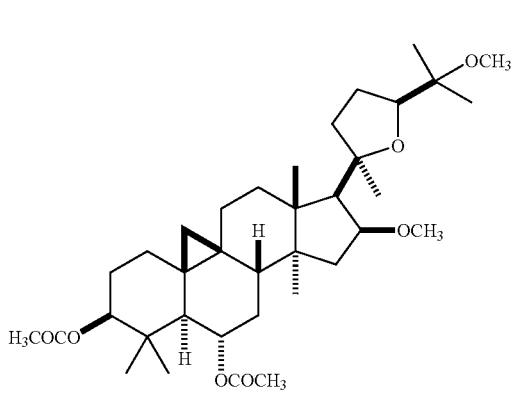

16

To a solution of 14 (30 mg, 0.052 mmol) in dimethylformamide (3 mL) were added iodomethane (0.75 mL, 12 mmol) and sodium hydride (60% oil dispersion, 40 mg, 1.0 mmol) at 0° C. under nitrogen, and the mixture was stirred at room temperature overnight. Water was added, and the mixture was extracted with ethyl acetate. The organic layer was washed with water and brine and dried on anhydrous sodium sulfate. The solvent was removed under reduced pressure and the residue was purified by silica gel column chromatography (4:1 hexane/ethyl acetate) to afford the compound 16 (29 mg, 92%).

ESI-MS m/z 603 (M+H)$^+$ $C_{36}H_{58}O_7$=602. $^1$H NMR (400 MHz, CDCl$_3$) δ (ppm) 0.33 (d, J=4.7 Hz, 1H), 0.56 (d, J=4.7 Hz, 1H), 0.82 (s, 3H), 0.89 (s, 3H), 0.96 (s, 3H), 1.06 (s, 3H), 1.1-1.9 (m, 17H), 1.13 (s, 3H), 1.19 (s, 3H), 1.23 (s, 3H), 1.97 (s, 3H), 2.02 (s, 3H), 2.3-2.4 (m, 2H), 3.05 (s, 3H), 3.23 (s, 3H), 3.81 (dd, J=9.0, 6.6 Hz, 1H), 3.95 (td, J=7.8, 5.1 Hz, 1H), 4.54 (dd, J=10.9, 4.7 Hz, 1H), 4.70 (td, J=9.4, 4.3 Hz, 1H).

Example 7C

Preparation of 16,25-dimethoxy Cycloastragenol, 17: Removal of Acetyl Groups from 16

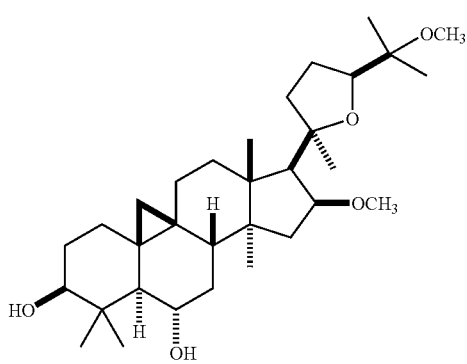

17

A mixture of 16 (28 mg, 0.046 mmol) and sodium methoxide (0.5 mol/L in methanol, 6 mL) was stirred at room temperature for 48 h. Water was added, and the mixture was extracted with ethyl acetate. The organic layer was washed with water and brine and dried on anhydrous sodium sulfate. The solvent was removed under reduced pressure, and the residue was purified by silica gel column chromatography (2:3 hexane/ethyl acetate) to afford the dimethoxy diol compound 17 (23 mg, 96%).

ESI-MS m/z 519 (M+H)$^+$ $C_{32}H_{54}O_5$=518. $^1$H NMR (400 MHz, CDCl$_3$) δ (ppm) 0.32 (d, J=4.7 Hz, 1H), 0.47 (d, J=4.3 Hz, 1H), 0.90 (s, 3H), 0.93 (s, 3H), 1.06 (s, 3H), 1.1-1.9 (m, 17H), 1.13 (s, 3H), 1.20 (s, 3H), 1.22 (s, 3H), 1.23 (s, 3H), 2.3-2.4 (m, 2H), 3.06 (s, 3H), 3.23 (s, 3H), 3.27 (m, 1H), 3.51 (td, J=9.4, 3.5 Hz, 1H), 3.81 (dd, J=9.4, 6.6 Hz, 1H), 3.96 (td, J=7.8, 5.5 Hz, 1H).

Example 7D

Alkylation of 3,6-diacetyl Cycloastragenol (14), with Retention of Acetyl Groups

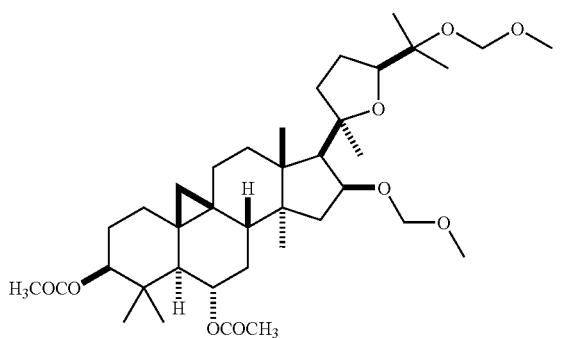

18

To a solution of 14 (109 mg, 0.190 mmol) in dichloromethane (10 mL) were added diisopropylethylamine (1.0 mL) and chloromethyl methyl ether (0.5 mL), and the mixture was stirred at room temperature for 24 h. Water was added, and the mixture was extracted with ethyl acetate. The organic layer was washed with water and brine and dried on anhydrous sodium sulfate. The solvent was removed under reduced pressure, and the residue was purified by silica gel column chromatography (3:1 hexane/ethyl acetate) to give the compound 18 (114 mg, 90%).

$^1$H NMR (400 MHz, CDCl$_3$) δ (ppm) 0.31 (d, J=5.1 Hz, 1H), 0.56 (d, J=4.7 Hz, 1H), 0.80 (s, 3H), 0.88 (s, 3H), 0.96 (s, 3H), 1.1-2.0 (m, 18H), 1.15 (s, 3H), 1.17 (s, 3H), 1.28 (s, 3H), 1.34 (s, 3H), 1.96 (s, 3H), 2.02 (s, 3H), 2.28 (d, J=8.2 Hz, 1H), 3.30 (s, 3H), 3.33 (s, 3H), 3.81 (t, J=7.2 z, 1H), 4.17 (m, 1H), 4.5-4.6 (m, 3H), 4.7-4.8 (m, 3H).

Example 7E

Removal of Acetyl Groups from 18

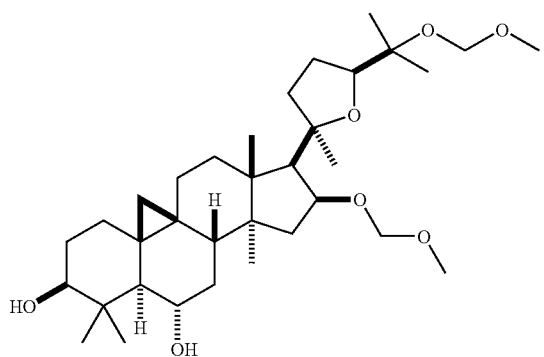

19

A mixture of 18, above (3,6-diacetyl-16,25-di(methoxymethyl)ether derivative of cycloastragenol) (102 mg, 0.150 mmol) and sodium methoxide (0.5 mol/L in methanol, 10 mL) was stirred at room temperature for 48 h. Water was added, and the mixture was extracted with ethyl acetate. The organic layer was washed with water and brine and dried on anhydrous sodium sulfate. The solvent was removed under reduced pressure, and the residue was purified by silica gel column chromatography (1:1 hexane/ethyl acetate) to afford the di(methoxymethyl)ether compound 19 (80 mg, 92%).

ESI-MS m/z 579 (M+H)$^+$ $C_{34}H_{58}O_7$=578. $^1$H NMR (400 MHz, CDCl$_3$) δ (ppm) 0.32 (d, J=4.7 Hz, 1H), 0.48 (d, J=4.3 Hz, 1H), 0.89 (s, 3H), 0.93 (s, 3H), 1.1-2.0 (m, 18H), 1.15 (s, 3H), 1.17 (s, 3H), 1.22 (s, 3H), 1.29 (s, 3H), 1.34 (s, 3H), 2.29 (d, J=8.6 Hz, 1H), 3.28 (m, 1H), 3.30 (s, 3H), 3.33 (s, 3H), 3.53 (m, 1H), 3.81 (t, J=7.2 Hz, 1H), 4.18 (td, J=7.8, 5.5 Hz, 1H), 4.50 (d, J=6.6 Hz, 1H), 4.54 (d, J=6.2 Hz, 1H), 4.71 (d, J=7.0 Hz, 1H), 4.76 (d, J=7.4 Hz, 1H).

Example 8

Alkylation of Triacetyl Cycloastragenol 15, Followed by Removal of Acetyl Groups

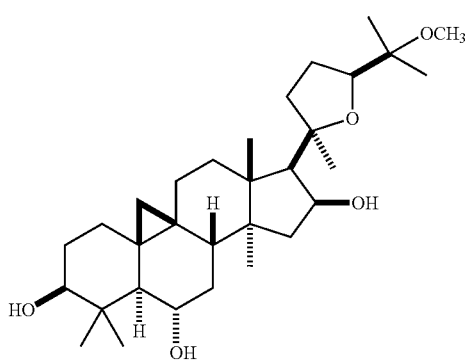

20

To a solution of 15 (30 mg, 0.049 mmol) in dimethylformamide (3 mL) were added added iodomethane (0.75 mL, 12 mmol) and sodium hydride (60% oil dispersion, 40 mg, 1.0 mmol) at 0° C. under nitrogen, and the mixture was stirred at room temperature overnight. Water was added, and the mixture was extracted with ethyl acetate. The organic layer was washed with water and brine and dried on anhydrous sodium sulfate. The solvent was removed under reduced pressure.

To the residue was added sodium methoxide in methanol (0.5 mol/L, 6 mL), and the mixture was stirred at room temperature overnight. 10% Hydrochloric acid was added, and the mixture was extracted with ethyl acetate. The organic layer was washed with water and brine and dried on anhydrous sodium sulfate. The solvent was removed under reduced pressure, and the residue was purified by silica gel column chromatography (1:2 hexane/ethyl acetate) to afford 20 (23 mg, 93%).

ESI-MS m/z 505 (M+H)$^+$ $C_{31}H_{52}O_5$=504. $^1$H NMR (400 MHz, CDCl$_3$) δ (ppm) 0.33 (d, J=4.3 Hz, 1H), 0.48 (d, J=4.3 Hz, 1H), 0.8-2.1 (m, 17H), 0.91 (s, 3H), 0.93 (s, 3H), 1.04 (s, 3H), 1.14 (s, 3H), 1.20 (s, 3H), 1.22 (s, 3H), 1.23 (s, 3H), 2.28 (d, J$_1$=7.8 Hz, 1H), 2.60 (q, J=10.9 Hz, 1H), 3.17 (s, 3H), 3.27 (m, 1H), 3.51 (td, J=9.8, 3.5 Hz, 1H), 3.72 (dd, J=9.0, 5.5 Hz, 1H), 4.62 (m, 1H).

Example 9A

Alkylation of Free Hydroxyls of Cycloastragenol Monoglycoside 6

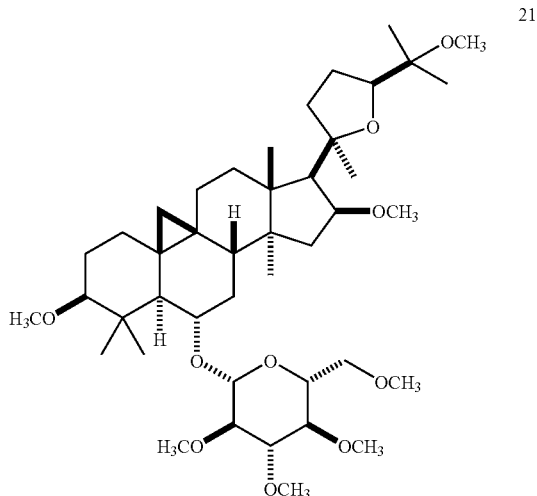

21

To a solution of 6 (50 mg, 0.077 mmol) in dimethylformamide (4 mL) were added iodomethane (1.0 mL, 16 mmol) and sodium hydride (60% oil dispersion, 60 mg, 1.5 mmol) at 0° C. under nitrogen, and the mixture was stirred at room temperature overnight. Water was added, and the mixture was extracted with ethyl acetate. The organic layer was washed with water and brine and dried on anhydrous sodium sulfate. The solvent was removed under reduced pressure, and the residue was purified by silica gel column chromatography (3:1 hexane/ethyl acetate) to afford permethoxy compound 21 (33 mg, 57%).

ESI-MS m/z 751 (M+H)$^+$ $C_{43}H_{74}O_{10}$=750. $^1$H NMR (400 MHz, CDCl$_3$) δ (ppm) 0.21 (d, J=4.7 Hz, 1H), 0.47 (d, J=4.3 Hz, 1H), 0.8-2.0 (m, 17H), 0.87 (s, 3H), 0.89 (s, 3H), 1.05 (s, 3H), 1.13 (s, 3H), 1.17 (s, 3H), 1.22 (s, 3H), 2.3-2.4 (m, 2H), 2.67 (dd, J=11.0, 4.1 Hz, 1H), 2.92 (t, J=8.2 Hz, 1H), 3.06 (s, 3H), 3.1-3.6 (m, 6H), 3.22 (s, 3H), 3.32 (s, 3H), 3.35 (s, 3H), 3.48 (s, 3H), 3.49 (s, 3H), 3.59 (s, 3H), 3.80 (dd, J=9.0, 6.6 Hz, 1H), 3.94 (m, 1H), 4.24 (d, J=7.4 Hz, 1H).

Example 9B

Preparation of 3,16,25-trimethoxy Astragenol, 22: Removal of Glycoside from Permethoxy Compound 21, with Concomitant Rearrangement

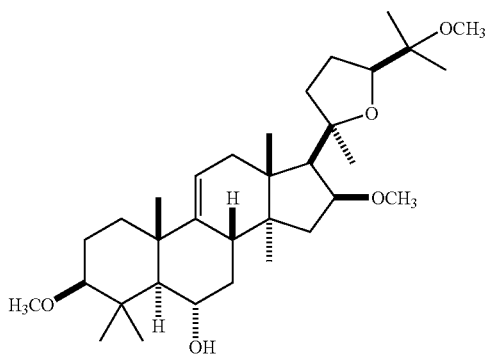

To a solution of 21 (30 mg, 0.040 mmol) in methanol (10 mL) was added sulfuric acid (0.2 mL), and the mixture was refluxed for 10 h. Water was added, and the mixture was extracted with ethyl acetate. The organic layer was washed with water and brine and dried on anhydrous sodium sulfate. The solvent was removed under reduced pressure, and the residue was purified by silica gel column chromatography (4:1 hexane/ethyl acetate) to afford 22 (3.6 mg, 17%).

ESI-MS m/z 533 (M+H)$^+$ $C_{33}H_{56}O_5$=532. $^1$H NMR (400 MHz, CDCl$_3$) δ (ppm) 0.73 (s, 3H), 0.8-2.0 (m, 18H), 0.85 (s, 3H), 1.00 (s, 3H), 1.03 (s, 3H), 1.06 (s, 3H), 1.14 (s, 3H), 1.24 (s, 3H), 1.25 (s, 3H), 2.3-2.4 (m, 2H), 2.58 (dd, J=10.9, 3.9 Hz, 1H), 3.09 (s, 3H), 3.24 (s, 3H), 3.34 (s, 3H), 3.80 (dd, J=9.4, 6.6 Hz, 1H), 3.98 (m, 1H), 5.25 (br d, J=5.5 Hz, 1H).

Example 10A

Alkylation of Free Hydroxyls of Cycloastragenol Monoglycoside 7

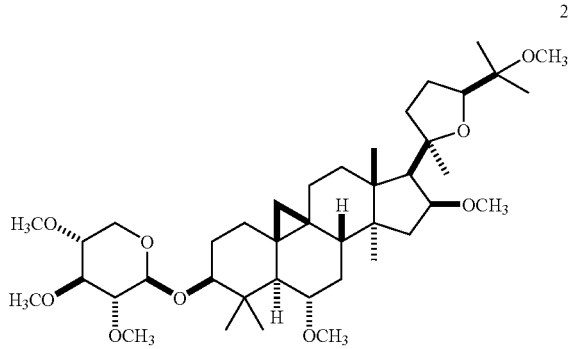

Compound 23 (18 mg, 53%) was obtained from 7 (30 mg) according to the procedure used for preparation of compound 21, above.

ESI-MS m/z 707 (M+H)$^+$ $C_{41}H_{70}O_9$=706. $^1$H NMR (400 MHz, CDCl$_3$) δ (ppm) 0.20 (d, J=4.3 Hz, 1H), 0.44 (d, J=4.3 Hz, 1H), 0.8-1.9 (m, 17H), 0.90 (s, 3H), 0.93 (s, 3H), 1.05 (s, 3H), 1.11 (s, 3H), 1.13 (s, 3H), 1.18 (s, 3H), 1.23 (s, 3H), 2.3-2.4 (m, 2H), 2.9-3.6 (m, 6H), 3.09 (s, 3H), 3.20 (s, 3H), 3.22 (s, 3H), 3.42 (s, 3H), 3.58 (s, 3H), 3.59 (s, 3H), 3.80 (dd, J=9.0, 6.6 Hz, 1H), 3.9-4.0 (m, 2H), 4.21 (d, J=7.4 Hz, 1H).

Example 10B

Preparation of 6,16,25-trimethoxy Astragenol, 24: Removal of Glycoside from Permethoxy Compound 23, with Concomitant Rearrangement

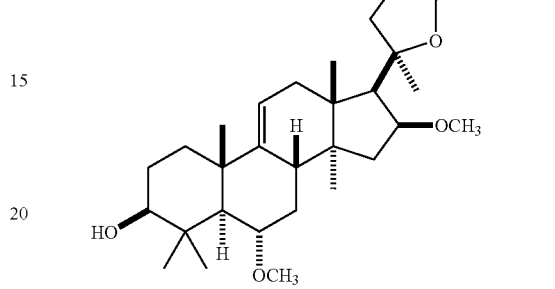

Compound 24 (7.1 mg, 56%) was obtained from 23 (17 mg) according to the procedure used for preparation of compound 22, above.

ESI-MS m/z 533 (M+H)$^+$ $C_{33}H_{56}O_5$=532. $^1$H NMR (400 MHz, CDCl$_3$) δ (ppm) 0.74 (s, 3H), 0.8-2.4 (m, 18H), 0.85 (s, 3H), 0.92 (s, 3H), 1.03 (s, 3H), 1.06 (s, 3H), 1.14 (s, 3H), 1.23 (s, 3H), 1.24 (s, 3H), 3.10 (s, 3H), 3.18 (m, 1H), 3.23 (s, 3H), 3.34 (s, 3H), 3.53 (m, 1H), 3.80 (dd, J=9.4, 6.6 Hz, 1H), 3.97 (m, 1H), 5.24 (d, J=5.5 Hz, 1H).

Example 11

Preparation of 3,6-dimethoxy Cycloastragenol 25: Methylation of 16,25-di (methoxymethyl)ether Compound 19, with Removal of di(methoxymethyl)ether Groups

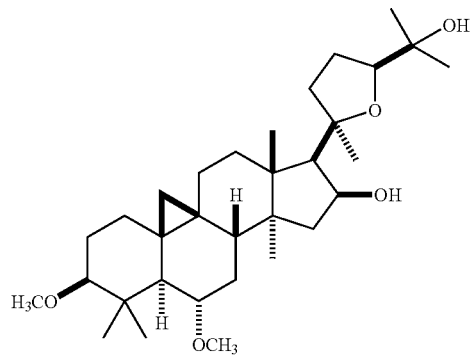

To a solution of 19 (30 mg, 0.052 mmol) in dimethylformamide (3 mL) were added iodomethane (0.75 mL, 12 mmol) and sodium hydride (60% oil dispersion, 40 mg, 1.0 mmol) at 0° C. under nitrogen, and the mixture was stirred at room temperature overnight. Water was added, and the mixture was extracted with ethyl acetate. The organic layer was washed with water and brine and dried on anhydrous sodium sulfate. The solvent was removed under reduced pressure.

To this residue were added tetrahydrofuran (5 mL) and 10% hydrochloric acid (1 mL), and the mixture was stirred at room temperature overnight, then refluxed for 1 h. Water was added, and the mixture was extracted with ethyl acetate. The organic layer was washed with water and brine and dried on anhydrous sodium sulfate. The solvent was removed under reduced pressure, and the residue was purified by silica gel column chromatography (3:1~1:1 hexane/ethyl acetate) to afford 25 (13 mg, 48%) and a smaller amount (7.4 mg, 25%) of the 3,6-dimethoxy-16-(methoxymethyl)ether compound 26.

25: ESI-MS m/z 563 (M+H)$^+$ $C_{34}H_{58}O_6$=562. $^1$H NMR (400 MHz, CDCl$_3$) δ (ppm) 0.19 (d, J=4.7 Hz, 1H), 0.45 (J=4.3 Hz, 1H), 0.8-2.3 (m, 18H), 0.86 (s, 3H), 0.92 (s, 3H), 1.05 (s, 3H), 1.07 (s, 3H), 1.20 (s, 3H), 1.24 (s, 3H), 1.28 (s, 3H), 2.41 (d, J=8.2 Hz, 1H), 2.70 (dd, J=11.1, 4.5 Hz, 1H), 2.90 (m, 1H), 3.19 (s, 3H), 3.326 (s, 3H), 3.330 (s, 3H), 3.71 (t, J=7.4 Hz, 1H), 4.37 (m, 1H), 4.53 (d, J=6.2 Hz, 1H), 4.59 (d, J=6.2 Hz, 1H).

26: ESI-MS m/z 519 (M+H)$^+$ $C_{32}H_{54}O_5$=518. $^1$H NMR (400 MHz, CDCl$_3$) δ (ppm) 0.21 (d, J=4.3 Hz, 1H), 0.45 (d, J=4.3 Hz, 1H), 0.8-2.0 (m, 17H), 0.86 (s, 3H), 0.93 (s, 3H), 1.06 (s, 3H), 1.12 (s, 3H), 1.20 (s, 3H), 1.21 (s, 3H), 1.28 (s, 3H), 2.30 (d, J=7.8 Hz, 1H), 2.54 (q, J=10.2 Hz, 1H), 2.69 (dd, J=11.3, 4.3 Hz, 1H), 2.89 (td, J=8.2, 4.3 Hz, 1H), 3.19 (s, 3H), 3.32 (s, 3H), 3.72 (t, J=7.2 Hz, 1H), 4.66 (m, 1H).

It is claimed:

1. A method of increasing telomerase activity in a cell or tissue, comprising:
    identifying a cell or tissue in which an increase in telomerase activity is desired, and
    contacting said cell or tissue with a formulation of an effective amount of an isolated compound of formula I:

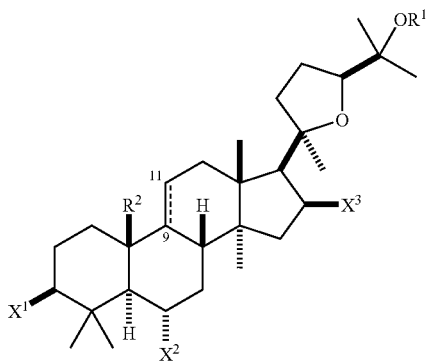

where:
    $X^1$ is hydroxy; or β-D-xylopyranoside;
    $X^2$ is hydroxy or β-D-glucopyranoside;
    $X^3$ is hydroxy or keto;
    OR' is hydroxy; and
    $R^2$ is methyl and ═ represents a double bond between carbons 9 and 11; or, $R^2$ forms, together with carbon 9, a fused cyclopropyl ring, and ═ represents a single bond between carbons 9 and 11 wherein telomerase activity is increased.

2. The method of claim 1, wherein said compound includes zero, one, or two glycosides.

3. The method of claim 2, wherein said compound includes zero or two glycosides.

4. The method of claim 1, wherein $R^2$ forms, together with carbon 9, a fused cyclopropyl ring, and ═ represents a single bond between carbons 9 and 11.

5. The method of claim 1, wherein $X^3$ is hydroxy.

6. The method of claim 1, wherein $X^1$ is OH and $X^2$ is OH.

7. The method of claim 1, wherein the compound is selected from astragaloside IV, cycloastragenol, astragenol, astragaloside IV 16-one, cycloastragenol 6-β-D-glucopyranoside, or cycloastragenol 3-β-D-xylopyranoside.

8. The method of claim 7, wherein the compound is selected from astragaloside IV, cycloastragenol, astragenol, or astragaloside IV 16-one.

9. The method of claim 8, wherein said compound is astragaloside IV.

10. The method of claim 8, wherein the compound is cycloastragenol.

11. The method of claim 8, wherein the compound is astragenol.

12. The method of claim 8, wherein the compound is astragaloside IV 16-one.

13. A method of increasing telomerase activity in a cell or tissue, in which an increase in telomerase activity is desired, comprising contacting said cell or tissue with a formulation comprising an effective amount of an isolated compound of formula I:

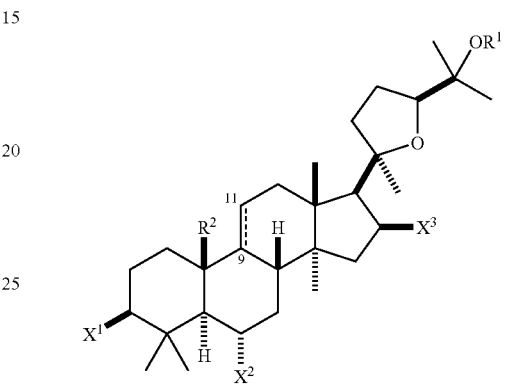

where:
    $X^1$ is hydroxy; or β-D-xylopyranoside;
    $X^2$ is hydroxy or β-D-glucopyranoside;
    $X^3$ is hydroxy or keto;
    OR' is hydroxy; and
    $R^2$ is methyl and ═ represents a double bond between carbons 9 and 11; or, $R^2$ forms, together with carbon 9, a fused cyclopropyl ring, and ═ represents a single bond between carbons 9 and 11 wherein telomerase activity is increased.

14. A method of increasing telomerase activity in a cell or tissue, in which an increase in telomerase activity is desired, comprising contacting said cell or tissue with a formulation comprising an effective amount of an isolated compound selected from cycloastragenol, astragenol, astragaloside IV 16-one, cycloastragenol 6-β-D-glucopyranoside, or cycloastragenol 3-β-D-xylopyranoside wherein telomerase activity is increased.

* * * * *